United States Patent
Shimai et al.

(10) Patent No.: US 11,058,343 B2
(45) Date of Patent: Jul. 13, 2021

(54) ELECTROCARDIOGRAPHIC WAVEFORM DISPLAY METHOD AND ELECTROCARDIOGRAM ANALYSIS DEVICE

(71) Applicant: Fukuda Denshi Co., Ltd., Tokyo (JP)

(72) Inventors: Yosuke Shimai, Tokyo (JP); Hironori Uchida, Tokyo (JP); Kenichi Sato, Tokyo (JP)

(73) Assignee: FUKUDA DENSHI CO., LTD., Tokyo (JP)

( * ) Notice: Subject to any disclaimer, the term of this patent is extended or adjusted under 35 U.S.C. 154(b) by 0 days.

(21) Appl. No.: 16/465,190

(22) PCT Filed: Nov. 30, 2017

(86) PCT No.: PCT/JP2017/043078
§ 371 (c)(1),
(2) Date: May 30, 2019

(87) PCT Pub. No.: WO2018/101412
PCT Pub. Date: Jun. 7, 2018

(65) Prior Publication Data
US 2020/0000357 A1   Jan. 2, 2020

(30) Foreign Application Priority Data
Nov. 30, 2016   (JP) .............................. JP2016-233323

(51) Int. Cl.
*G06F 3/048* (2013.01)
*A61B 5/316* (2021.01)
(Continued)

(52) U.S. Cl.
CPC .............. *A61B 5/316* (2021.01); *A61B 5/333* (2021.01); *A61B 5/339* (2021.01); *A61B 5/364* (2021.01);
(Continued)

(58) Field of Classification Search
CPC .......................... G06F 3/0482; G06F 3/04886
See application file for complete search history.

(56) References Cited

U.S. PATENT DOCUMENTS

| 2006/0100536 A1* | 5/2006 | Nagai | .................... | A61B 5/044 600/519 |
| 2012/0130220 A1* | 5/2012 | Maskara | ................ | A61N 1/056 600/374 |

(Continued)

FOREIGN PATENT DOCUMENTS

| JP | 11-216119 A | 8/1999 |
| JP | 2006-116207 A | 5/2006 |

(Continued)

OTHER PUBLICATIONS

International Search Report from International Application No. PCT/JP2017/043078 dated Dec. 26, 2017.

*Primary Examiner* — David E Choi
(74) *Attorney, Agent, or Firm* — Brundidge & Stanger, P.C.

(57) ABSTRACT

When a user uses a finger to press and hold a first candidate display area, the first candidate display area is enclosed in a selection frame (W1), a simple window (W10) is displayed, and analysis results relating to a first candidate segment waveform are displayed in this simple window (W10). Analysis results can therefore be confirmed without switching screens and, as a result, inspection results can be confirmed with fewer steps and an electrocardiographic waveform and analysis results therefor can be compared on the same screen.

12 Claims, 25 Drawing Sheets

(51) Int. Cl.
  *A61B 5/00* (2006.01)
  *G06F 3/0482* (2013.01)
  *G06F 3/0488* (2013.01)
  *A61B 5/333* (2021.01)
  *A61B 5/339* (2021.01)
  *A61B 5/364* (2021.01)

(52) U.S. Cl.
  CPC ............ *A61B 5/7203* (2013.01); *A61B 5/748* (2013.01); *G06F 3/0482* (2013.01); *G06F 3/04886* (2013.01); *G06F 2203/04804* (2013.01)

(56) References Cited

U.S. PATENT DOCUMENTS

| | | | | |
|---|---|---|---|---|
| 2013/0231578 | A1* | 9/2013 | Takayanagi | A61B 5/743 600/521 |
| 2014/0125477 | A1* | 5/2014 | Kasuya | A61B 5/044 340/525 |
| 2015/0235394 | A1* | 8/2015 | Ben-Oni | G06T 11/203 345/440.1 |
| 2015/0243040 | A1* | 8/2015 | Ben-Oni | G06T 11/206 345/629 |
| 2015/0250400 | A1* | 9/2015 | Takizawa | A61B 5/04012 600/510 |
| 2016/0095526 | A1* | 4/2016 | Yoshimura | A61B 5/044 600/523 |
| 2019/0279229 | A1* | 9/2019 | Warita | G06Q 30/02 |
| 2019/0350480 | A1* | 11/2019 | Riemenschneider | G16H 40/63 |
| 2020/0000354 | A1* | 1/2020 | Shimai | A61B 5/7435 |
| 2020/0000357 | A1* | 1/2020 | Shimai | G06F 3/0482 |

FOREIGN PATENT DOCUMENTS

| | | |
|---|---|---|
| JP | 2007-020799 A | 2/2007 |
| JP | 2007-190227 A | 8/2007 |
| JP | 2013208367 A | 10/2013 |
| WO | 2012099933 A2 | 7/2012 |

* cited by examiner

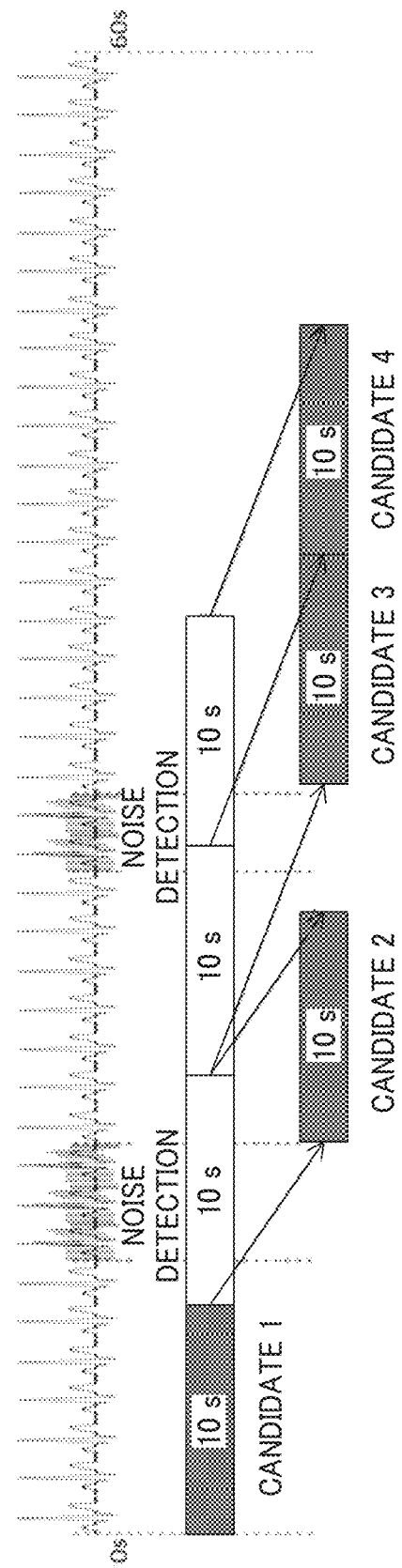

ELECTROCARDIOGRAPHIC WAVEFORM DISPLAY METHOD AND ELECTROCARDIOGRAM ANALYSIS DEVICE

TECHNICAL FIELD

The present invention relates to an electrocardiogram waveform display method and an electrocardiogram analyzing apparatus.

BACKGROUND ART

Conventionally, electrocardiograms have been widely used as a diagnostic indicator of heart disease. An electrocardiogram is obtained by detecting electrical activity of the heart on the body surface and representing it as the electrocardiogram waveform. Analysis of this electrocardiogram waveform (electrocardiogram) yields various types of information on heart activity.

In recent years, the development of digital electrocardiographs that digitalize and record electrocardiograms has made it possible to automatically analyze the electrocardiograms using a computer (see, for example, PTL 1).

With an electrocardiogram analyzing apparatus capable of such automatic analysis of electrocardiograms, a medical worker first applies an electrode on a subject, the electrocardiogram analyzing apparatus then collects electrocardiogram waveforms, and the electrocardiogram waveforms collected by the electrocardiogram analyzing apparatus are then automatically analyzed.

In the present specification, "collect" refers to temporarily storing the electrocardiogram waveforms of an analysis candidate, and "record" refers to recording the analyzed electrocardiogram waveforms and the analysis results.

CITATION LIST

Patent Literature

PTL 1
Japanese Patent Application Laid-Open No. 2006-116207

SUMMARY OF INVENTION

Technical Problem

By the way, in a conventional electrocardiogram analyzing apparatus, the analysis target waveform and the related analysis results are displayed on different screens. Therefore, when the user wants to see the analysis results related to a certain analysis target waveform, the user needs to switch the screen from the screen showing the analysis target waveform to the screen showing the analysis results. Incidentally, the analysis result screen shows one beat of a representative waveform of the analysis target waveform, and the related analysis results (analysis findings, measurement values, subject information, and examination information). When the user wants to see the analysis target waveform, which is the base of the analysis result screen, again from the analysis result screen, the user needs to switch the screen again from the screen showing the analysis results to the screen showing the analysis target waveform.

Repeating such screen switching leads to an increase in the number of operations by the user, which increases the burden on the user. On the other hand, when the analysis target waveform and the analysis results are printed out (report printing), the analysis target waveform and the related analysis results can be easily compared with each other. However, there has been a problem that report printing cannot be achieved at paperless facilities, for example.

The present invention, which has been made in consideration of the above points, provides an electrocardiogram waveform display method and an electrocardiogram analyzing apparatus that can present the relationship between an analysis target waveform and the related analysis results to the user with fewer operations and in an easy-to-understand manner.

Solution to Problem

One aspect of an electrocardiogram waveform display method of the present invention is a method used for an electrocardiogram analyzing apparatus, the method including: an analysis target waveform screen display step of displaying an electrocardiogram waveform to be analyzed, on an analysis target waveform screen; and an analysis result display step of displaying an analysis result related to the electrocardiogram waveform to be analyzed, simultaneously with the analysis target waveform screen according to an operation by a user.

One aspect of an electrocardiogram analyzing apparatus of the present invention includes: a display section; a display control section; a user operation section; and an arithmetic section that acquires an analysis result by analyzing an electrocardiogram waveform, in which the display control section displays an analysis result related to the electrocardiogram waveform, simultaneously with a screen showing a corresponding electrocardiogram waveform, according to an operation by a user on the user operation section.

Advantageous Effects of Invention

According to the present invention, the analysis results related to electrocardiogram waveforms to be analyzed are displayed simultaneously with an analysis target waveform screen, eliminating the need for switching the screens and allowing the electrocardiogram waveforms and the related analysis results to be viewed simultaneously. As a result, the relationship between the electrocardiogram waveforms to be analyzed and the related analysis results can be presented to the user with fewer operations and in an easy-to-understand manner.

BRIEF DESCRIPTION OF DRAWINGS

FIG. 10 is a diagram for explaining a method of extracting candidate segments excluding noise segments;

DESCRIPTION OF EMBODIMENTS

An embodiment of the present invention will be described below with reference to the accompanying drawings.

<1> Overall Configuration

Figure 1:
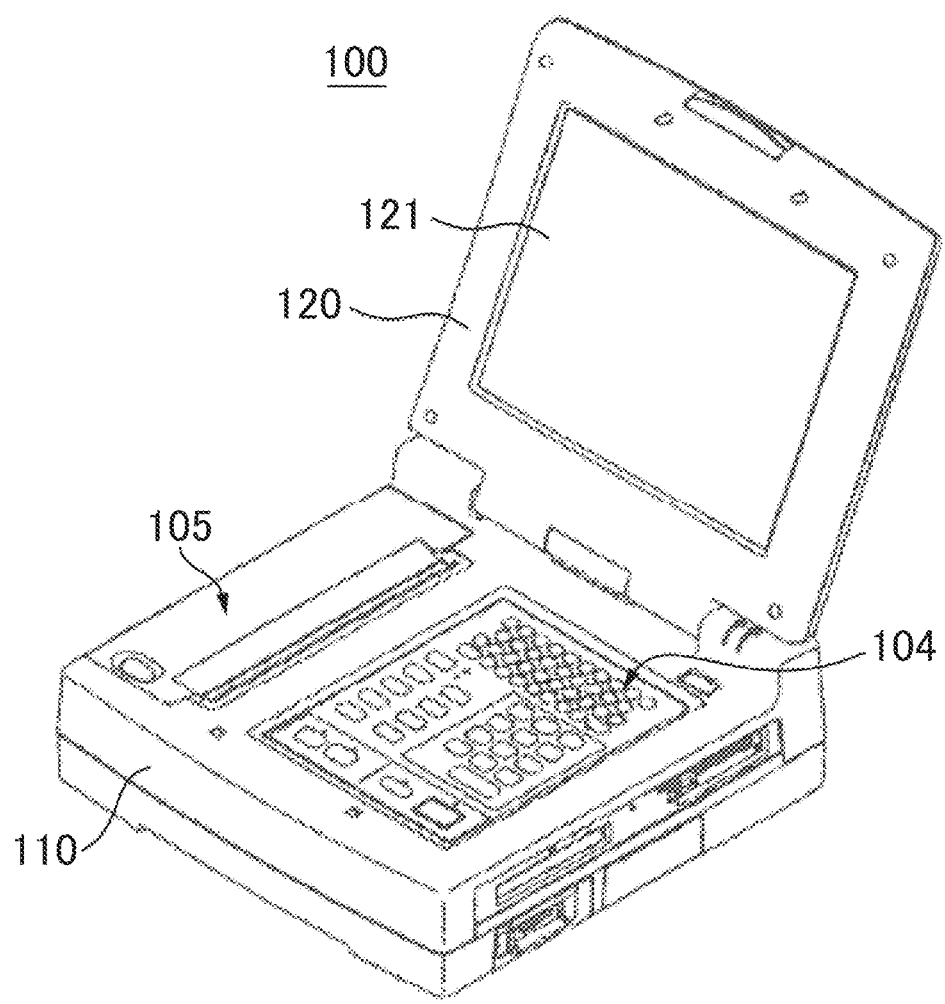
FIG. 1 is a perspective view showing the exterior configuration of an electrocardiograph of an embodiment.

FIG. 1 is a perspective view showing the exterior configuration of an electrocardiograph of this embodiment. Electrocardiograph 100 consists of body 110 and display section 120. Body 110 is provided with input keys 104 and printer section 105. Display section 120 is provided with touch screen 121.

In the case of this embodiment, the size of touch screen 121 is 15 inches. The 15-inch size roughly corresponds to the A4 paper size. Therefore, in electrocardiograph 100 of this embodiment, an electrocardiogram waveform having the same layout and size as those recorded on A4 size paper can be viewed on touch screen 121.

Figure 2:
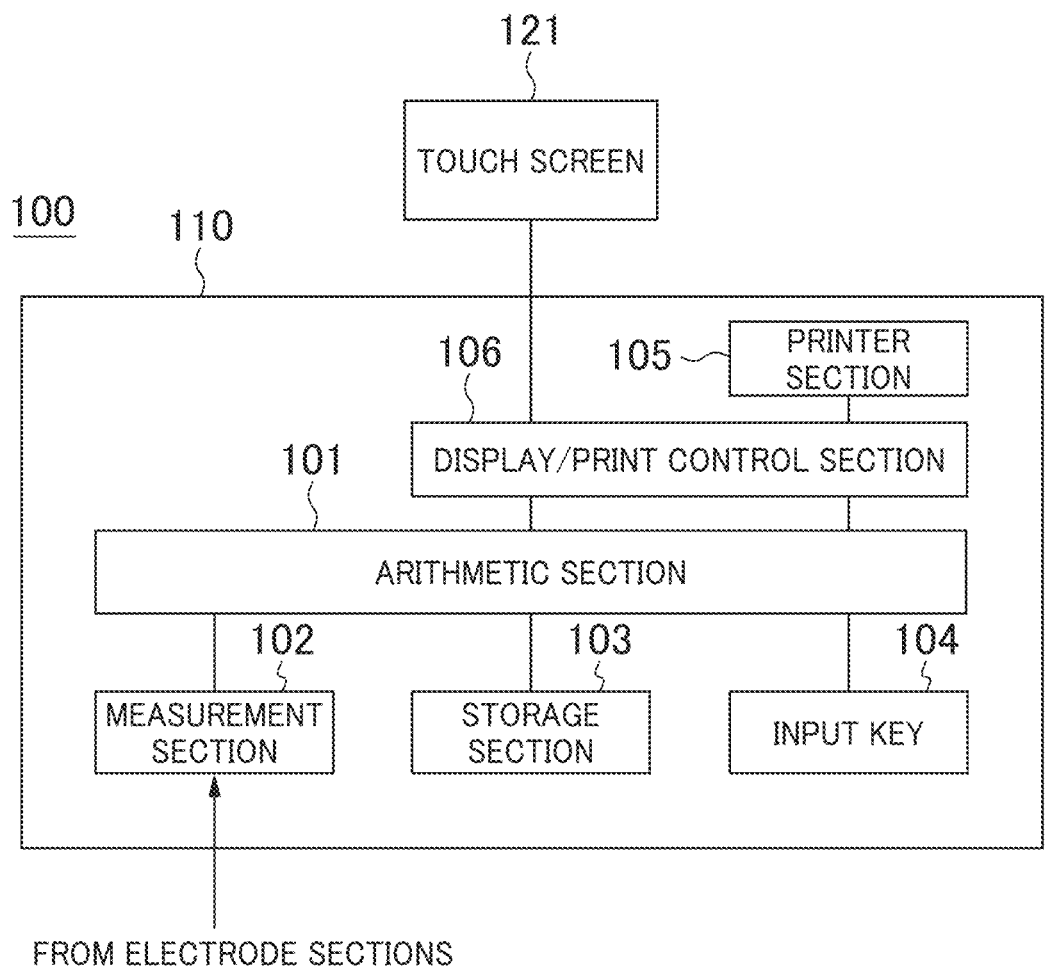
FIG. 2 is a block diagram showing the main configuration of an electrocardiograph.

FIG. 2 is a block diagram showing the main configuration of electrocardiograph 100. Body 110 includes arithmetic section 101, measurement section 102, storage section 103, input keys 104, printer section 105, and display/print control section 106.

Arithmetic section 101 is constituted of a central processing unit (CPU) or the like, and executes an electrocardiogram data processing program to form an electrocardiogram waveform, analyze the electrocardiogram waveform, and the like. In addition, arithmetic section 101 starts execution of the electrocardiogram data processing program, stops the execution, sets execution conditions (such as threshold values), controls various measurement instruments, such as measurement section 102, and controls various peripheral devices, such as touch screen 121 and printer section 105, according to the input commands.

Measurement section 102 is connected to an electrode section applied on a subject (that is, a subject of electrocardiographic measurement), performs amplification processing and the like on a measured voltage input from the electrode section, and outputs the processed measured voltage to arithmetic section 101. Incidentally, measurement section 102 is usually connected to electrode sections for limbs and electrode sections for a chest, and supplied with voltages needed to obtain a 12-lead electrocardiogram as inputs.

Storage section 103 consists of a hard disk drive, a semiconductor memory, and the like. Storage section 103 stores the data of electrocardiogram waveforms obtained by arithmetic section 101 and the analysis data thereof. Storage section 103 also stores measurement data output from measurement section 102.

Further, storage section 103 stores data on the settings of electrocardiograph 100 input by the user through touch screen 121 or input keys 104. Electrocardiograph 100 operates based on the data on the settings stored in storage section 103.

A menu screen and various setting screens are displayed on touch screen 121, and the user can select a menu and set various settings by touch operations on touch screen 121. Further, electrocardiogram waveforms, analysis results, and the like obtained by arithmetic section 101 are displayed on touch screen 121.

Printer section 105 is a laser printer, a thermal head printer, or the like, and prints the electrocardiogram waveforms and analysis results obtained by arithmetic section 101 according to an instruction from the user.

Display/print control section 106 controls the layout of the electrocardiogram waveforms displayed on the screen of touch screen 121 and printed on a recording sheet with printer section 105. The display of the electrocardiogram waveforms and the analysis results in this embodiment is controlled mainly by display/print control section 106.

<2> Examination Flow and Display on Screen During Examination

Next, an electrocardiogram analysis examination and screen display on electrocardiograph 100 in the case where electrocardiograph 100 of this embodiment is used will be described. Although the case where a standard 12-lead examination is performed as an electrocardiogram analysis examination will be described in this embodiment, the present invention can also be used for an electrocardiogram analysis examination other than the standard 12-lead examination.

Figure 3:
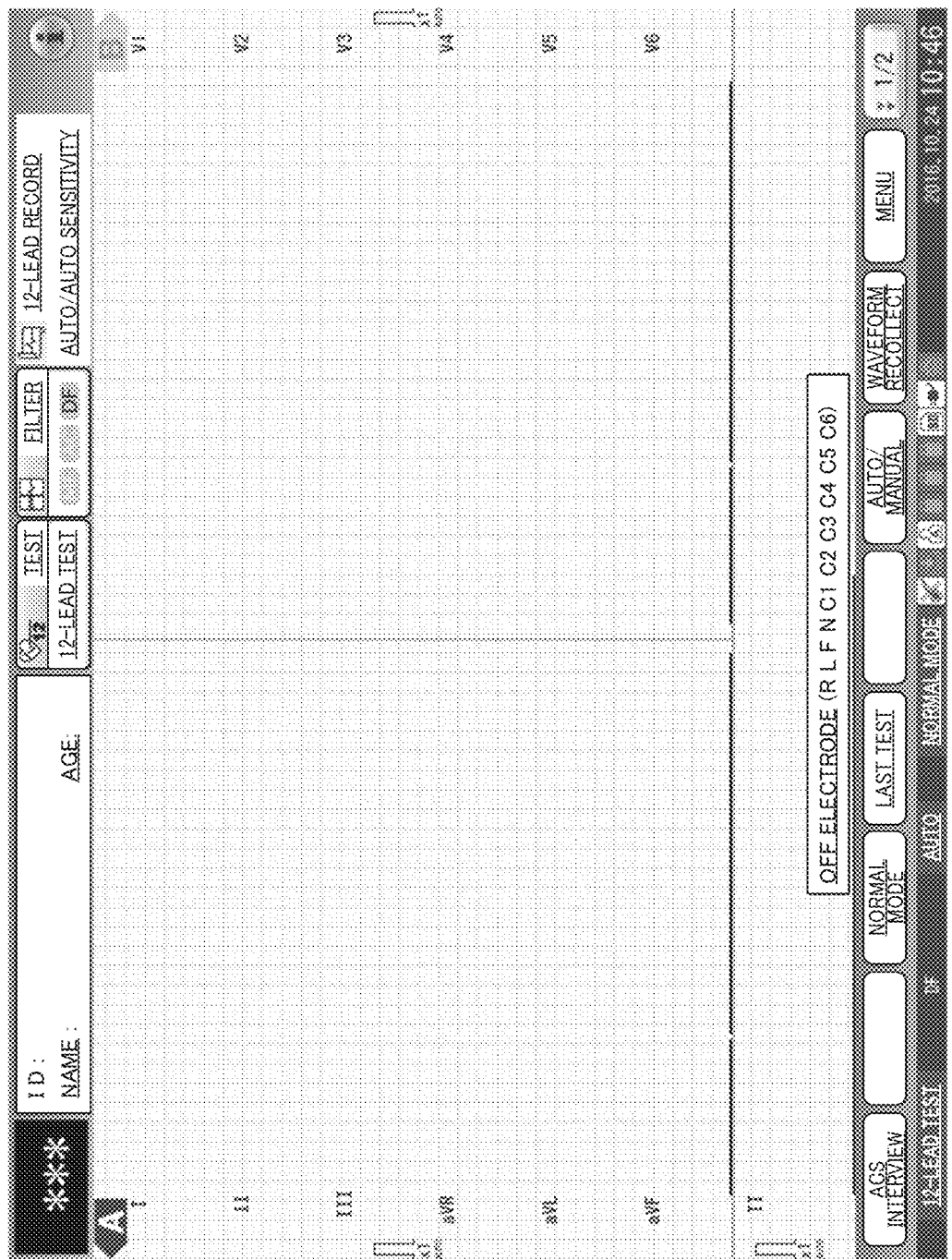
FIG. 3 is a diagram showing the initial screen of a 12-lead examination.
Figure 4:
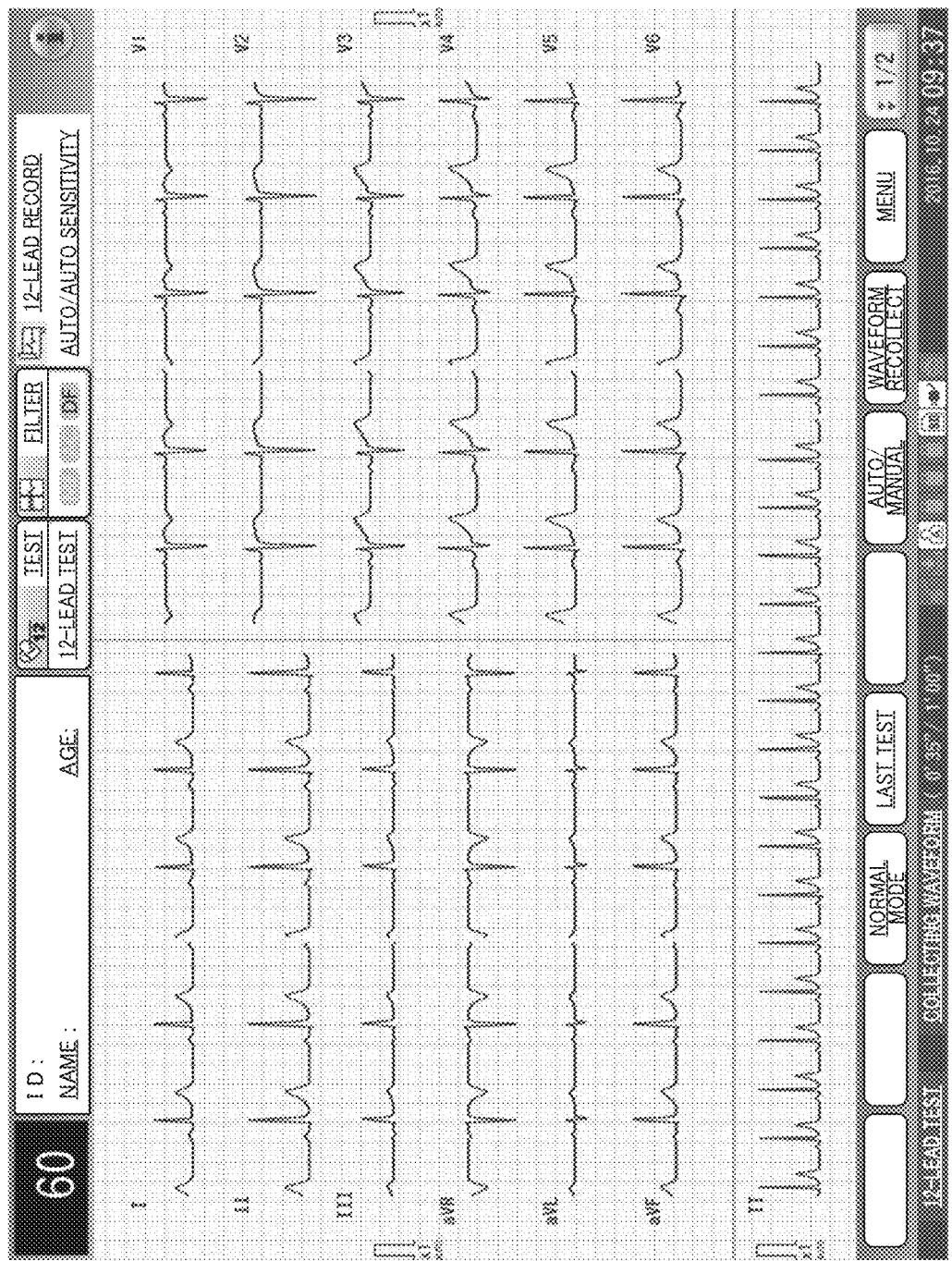
FIG. 4 is a diagram showing the screen that appears at the collection of electrocardiogram waveforms.

Upon start of the electrocardiogram analysis examination, the initial screen for a 12-lead examination shown in FIG. 3 is first displayed on touch screen 121. When electrodes are applied on a subject in this state, collection of electrocardiogram waveforms is started, and the electrocardiogram waveforms shown in FIG. 4 are displayed on touch screen 121. Here, the time for collecting the electrocardiogram waveforms can be set, for example, in the range of 30 seconds to 10 minutes (by seconds). This collection time corresponds to the waiting time until the completion of the collection, and when the collection time is set long, a large amount of electrocardiogram waveform data can be collected, which can improve the examination accuracy, while making the waiting time long. For this reason, the user sets the collection time taking these facts into consideration.

Upon completion of the collection of the waveforms, electrocardiograph 100 of this embodiment automatically extracts candidate waveforms, analyzes the waveforms, and displays candidate waveforms. To be specific, since the collected waveforms are stored in storage section 103, arithmetic section 101 extracts the waveforms of a plurality of candidate segments appropriate for analysis from the collected waveforms, and analyzes the waveforms of the extracted plurality of candidate segments. The waveforms of the extracted plurality of candidate segments are displayed on touch screen 121.

In this embodiment, a candidate segment refers to an analysis unit segment. In this embodiment, it is called a candidate segment because the user can make various selections on the analysis unit segment basis. Note that the processing for extracting the waveforms of a plurality of candidate segments through arithmetic section 101 will be explained in detail below.

Figure 5:
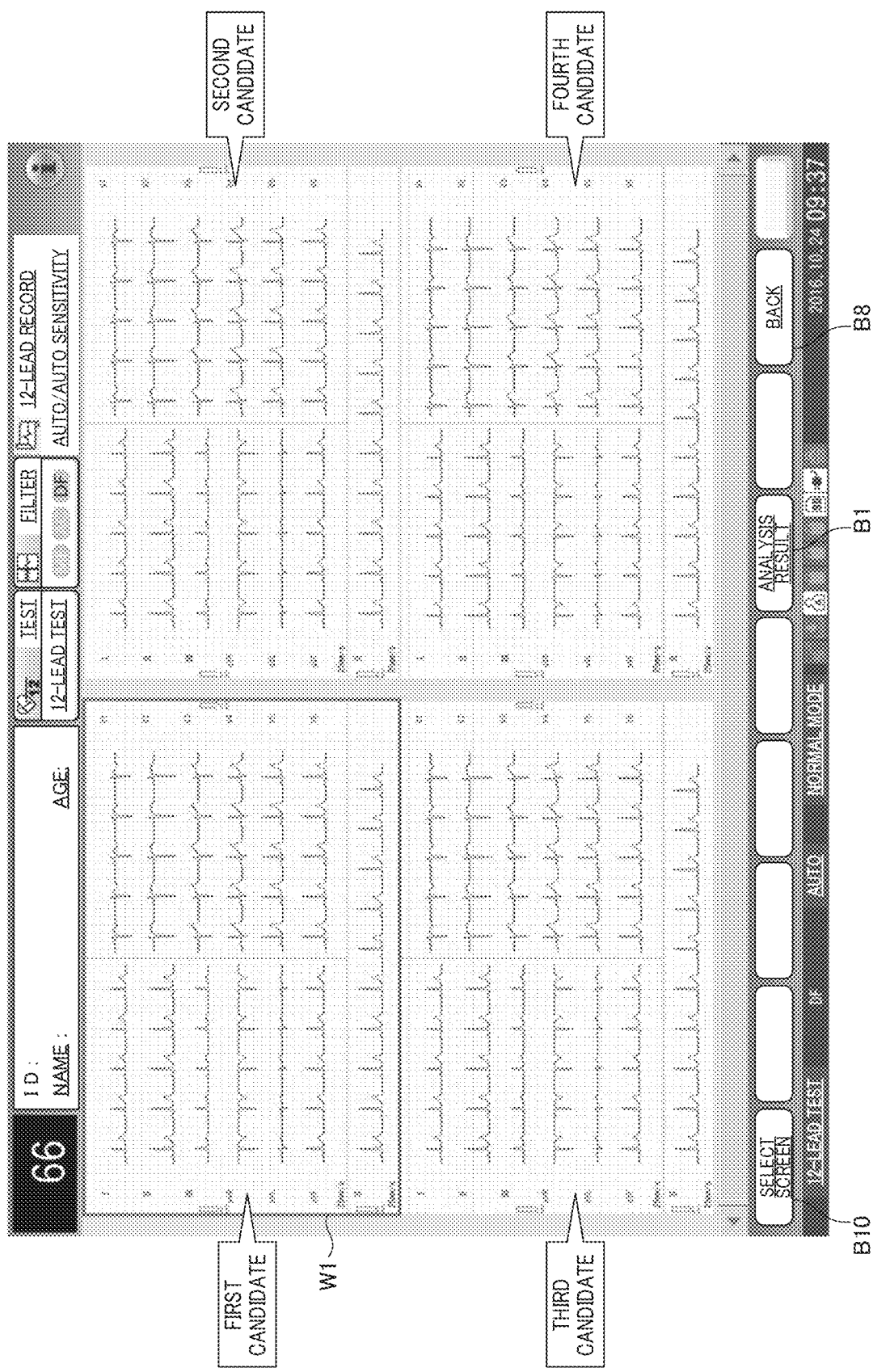
FIG. 5 is a diagram showing a candidate list screen.

FIG. 5 shows an example of a candidate list screen displayed on touch screen 121. In the example shown in FIG. 5, the waveform display area is divided into four so that four candidate segments for first to fourth candidates are displayed. To be specific, the first candidate is displayed at the upper left, the second candidate at the upper right, the third candidate at the lower left, and the fourth candidate at the lower right.

In this embodiment, the electrocardiogram waveforms of a plurality of candidate segments are displayed in one screen, allowing the user to compare a plurality of candidate segments in one screen and easily select the electrocardiogram waveform of the segment that should be recorded, from the plurality of candidate segments.

In this embodiment, the waveforms of the candidate segments from the first candidate to the fourth candidate are sorted in descending order of severity based on the analysis findings. This allows the user to see the waveforms in descending order of severity. By the way, when the severities are comparable, sorting in chronological ascending order is performed. Note that the sorting order is not limited to this, and sorting in chronological ascending order may be performed regardless of the severity, for example.

On the candidate list screen, one of the waveforms of the candidate segments is enclosed by selection frame W1. The display position of selection frame W1 can be selected by the user touching, with a finger, any one of the display areas in which the waveforms of the candidate segments of the first to fourth candidates are displayed. Although the waveform display area of the first candidate is enclosed by selection frame W1 in the example shown in FIG. 5, for example, touching the waveform display area of the second candidate causes the waveform display area of the second candidate to be enclosed by selection frame W1.

Although a selection on the display screen is made by touching with a finger in the description of the embodiments, needless to say, such a selection can be made by moving the pointer to the touching point and clicking the mouse instead of touching.

Figure 6:
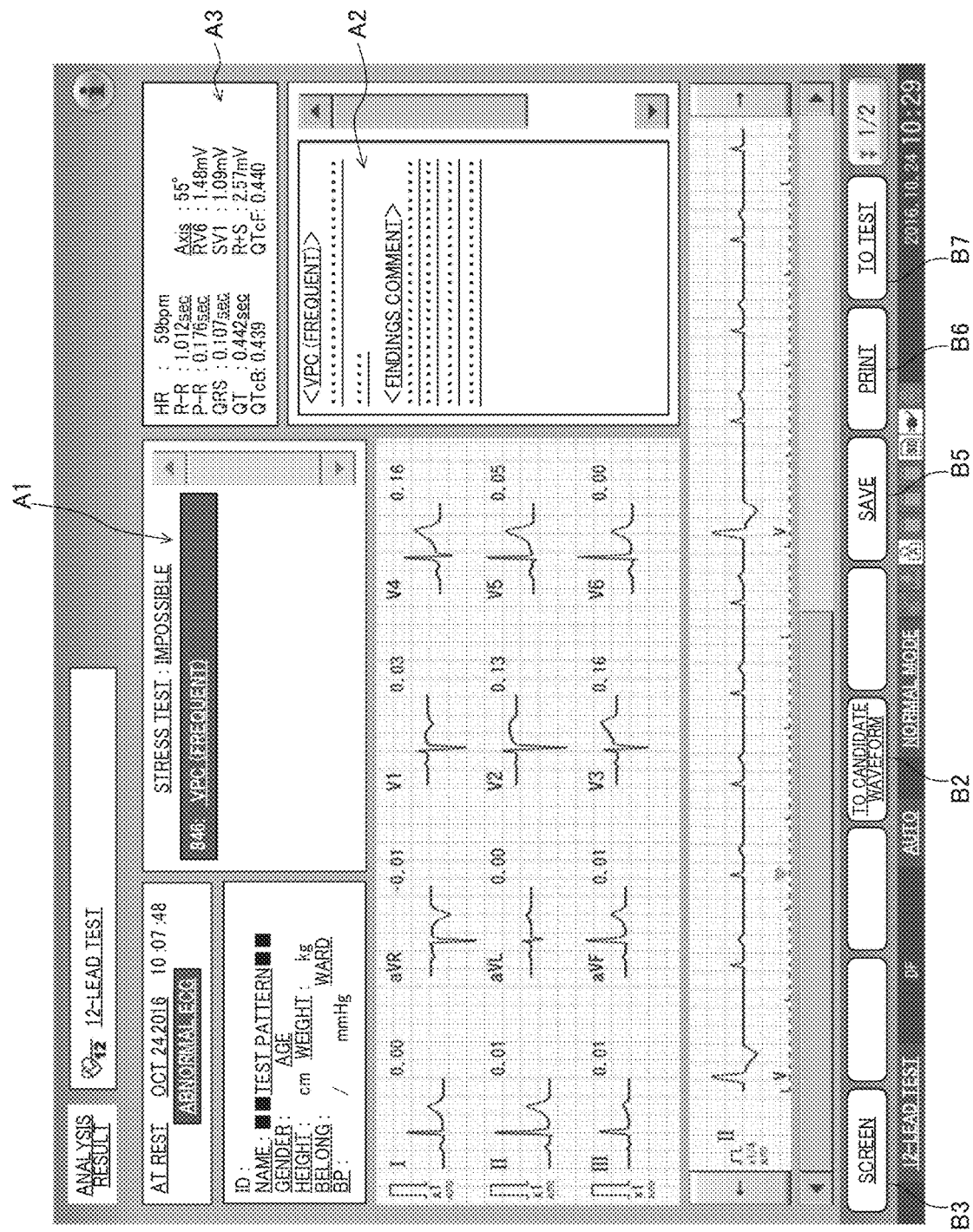
FIG. 6 is a diagram showing a screen showing the analysis results.

When the user touches analysis result button B1 on the candidate list screen shown in FIG. 5, an analysis result screen for the waveform enclosed by selection frame W1 is displayed. FIG. 6 shows an example of the destination analysis result screen. On the analysis result screen, finding A1, finding commentary A2, measurement value A3, and the like are shown. On the analysis result screen shown in FIG. 6, when the user touches "Go to candidate waveform" button B2, the candidate list screen shown in FIG. 5 is displayed again on the touch screen. Accordingly, the user can reselect a candidate waveform on the screen shown in FIG. 5.

Figure 7:
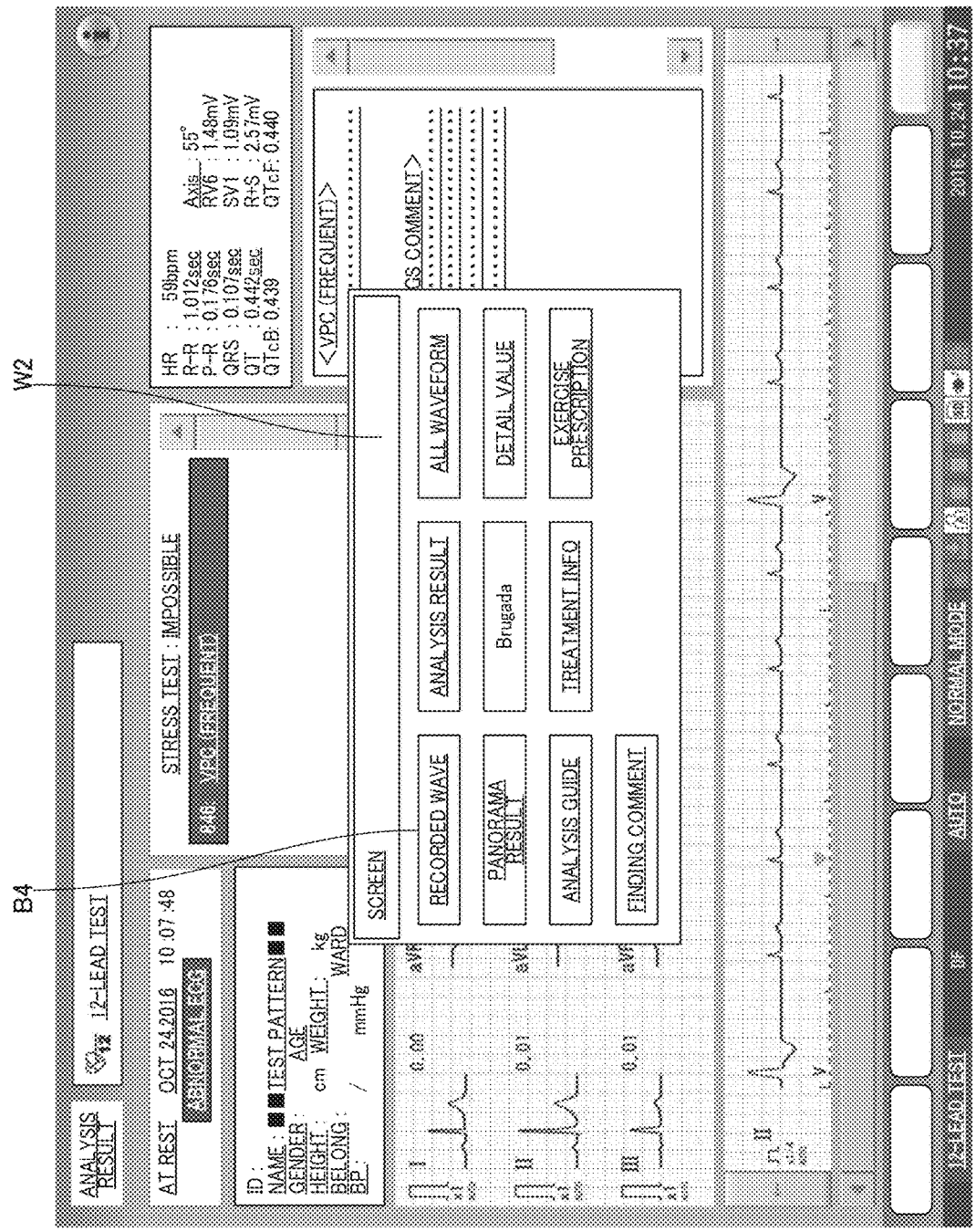
FIG. 7 is a diagram showing a screen with a window for switching screens popped up.
Figure 8:
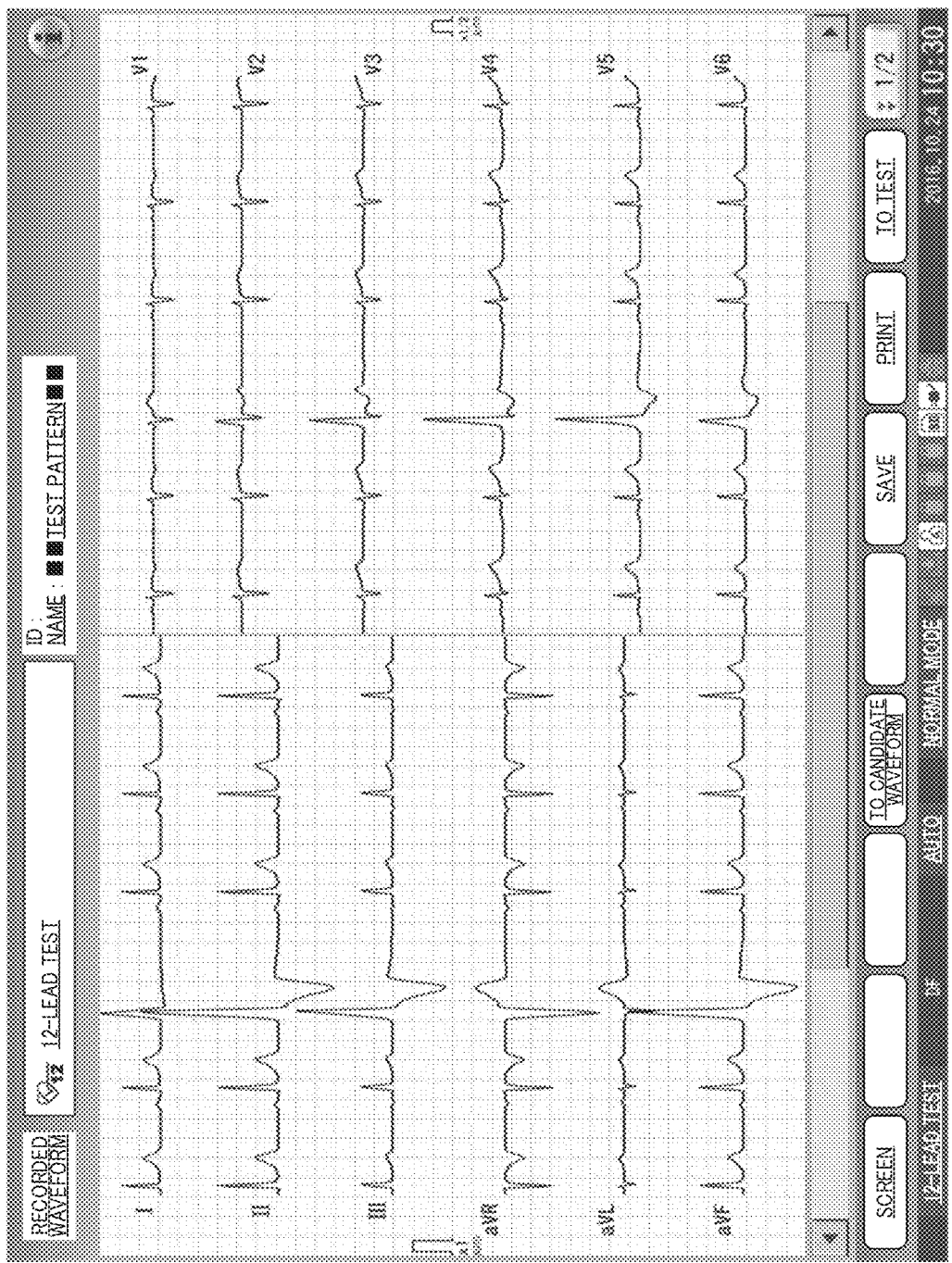
FIG. 8 is a diagram showing a screen showing recorded waveforms.

When the user touches "Screen" button B3 on the analysis result screen shown in FIG. 6, a screen with window W2 for switching screens popped up is displayed as shown in FIG. 7. When the user touches "Recorded waveform" button B4 in window W2, a recorded waveform screen is displayed as shown in FIG. 8. This recorded waveform screen is a screen for displaying a waveform obtained by resizing the waveform enclosed by selection frame W1 shown in FIG. 5 to the original recording size.

Touching "Save" button B5 on the analysis result screen shown in FIG. 6 causes electrocardiograph 100 to proceed to processing for saving the analysis results and waveform data of the currently selected candidate segment in storage section 103. Touching "Thermal" button B6 causes electrocardiograph 100 to proceed to processing for printing the analysis results of the currently selected candidate segment through printer section 105.

When the current examination should be terminated, for example, the user should touch "Go to examination" button B7 on the analysis result screen shown in FIG. 6 or touch "Return" button B8 on the candidate list screen shown in FIG. 5. Such an operation displays the initial screen shown in FIG. 3 on the touch screen.

<3> Change in Display Mode on Candidate List Screen

In this embodiment, the display mode of electrocardiogram waveforms on the candidate list screen can be changed. To be specific, the candidate list screen is sequentially changed as shown in FIGS. 9A to 9D in accordance with the number of times the user touches "Select screen" button B10 on the candidate list screen shown in FIG. 5.

Figure 9A:
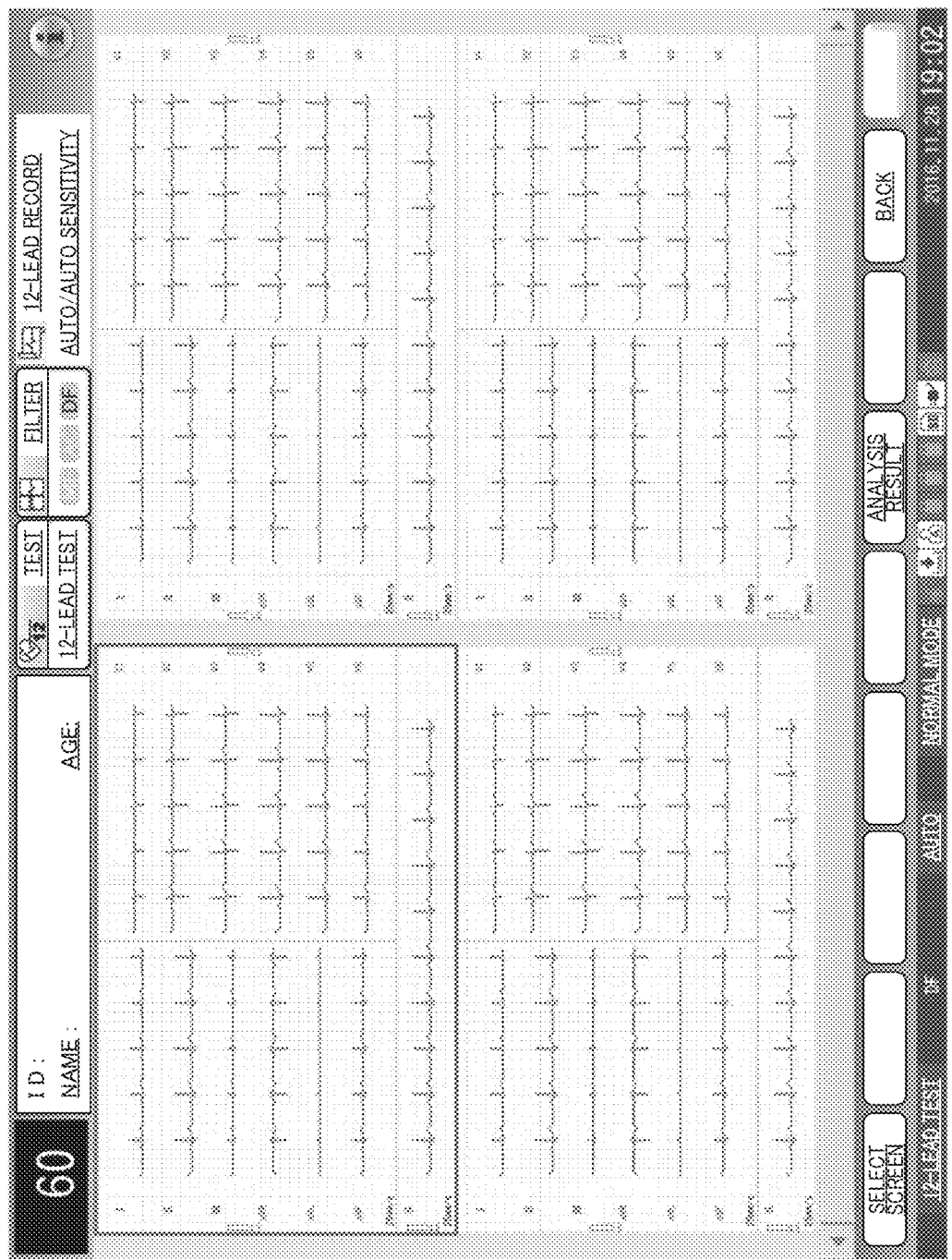
FIG. 9A is a diagram showing a candidate list screen on which the 12-lead electrocardiograms of (six channels×2) and the rhythm waveform of one channel are displayed for each candidate.

The candidate list screen shown in FIG. 9A shows a 12-lead electrocardiogram of (six channels×2) and a rhythm waveform of one channel in each candidate region (that is, one region that can be enclosed by selection frame W1). To be specific, the candidate list screen shown in FIG. 9A shows the electrocardiogram waveforms in the continuous mode or the coherent mode in each candidate region. In the case of electrocardiogram waveforms in the continuous mode or the coherent mode, among the 12-lead electrocardiogram waveforms, limb lead waveforms I, II, III, aVR, aVL, and aVF are disposed on the left side, and chest lead waveforms V1, V2, V3, V4, V5 and V6 are disposed on the right side. In the continuous mode, among the 10-second electrocardiogram waveforms, the limb lead waveforms in the first 0 to 5 seconds are displayed on the left side, and the chest lead waveforms in the following 5 to 10 seconds are displayed on the right side. On the other hand, in the coherent mode, among the 10-second waveforms, the limb lead waveforms in the first 0 to 5 seconds are displayed on the left side, and the chest lead waveforms in the first 0 to 5 seconds are displayed on the right side. In the continuous mode and the coherent mode, which are conventional display modes that have been widely used, electrocardiogram waveforms are disposed in such a manner that 12-lead waveforms can be collectively displayed on one screen of a limited size so that the user can easily diagnose with as little reduction as possible in the waveform amplitude.

Figure 9B:
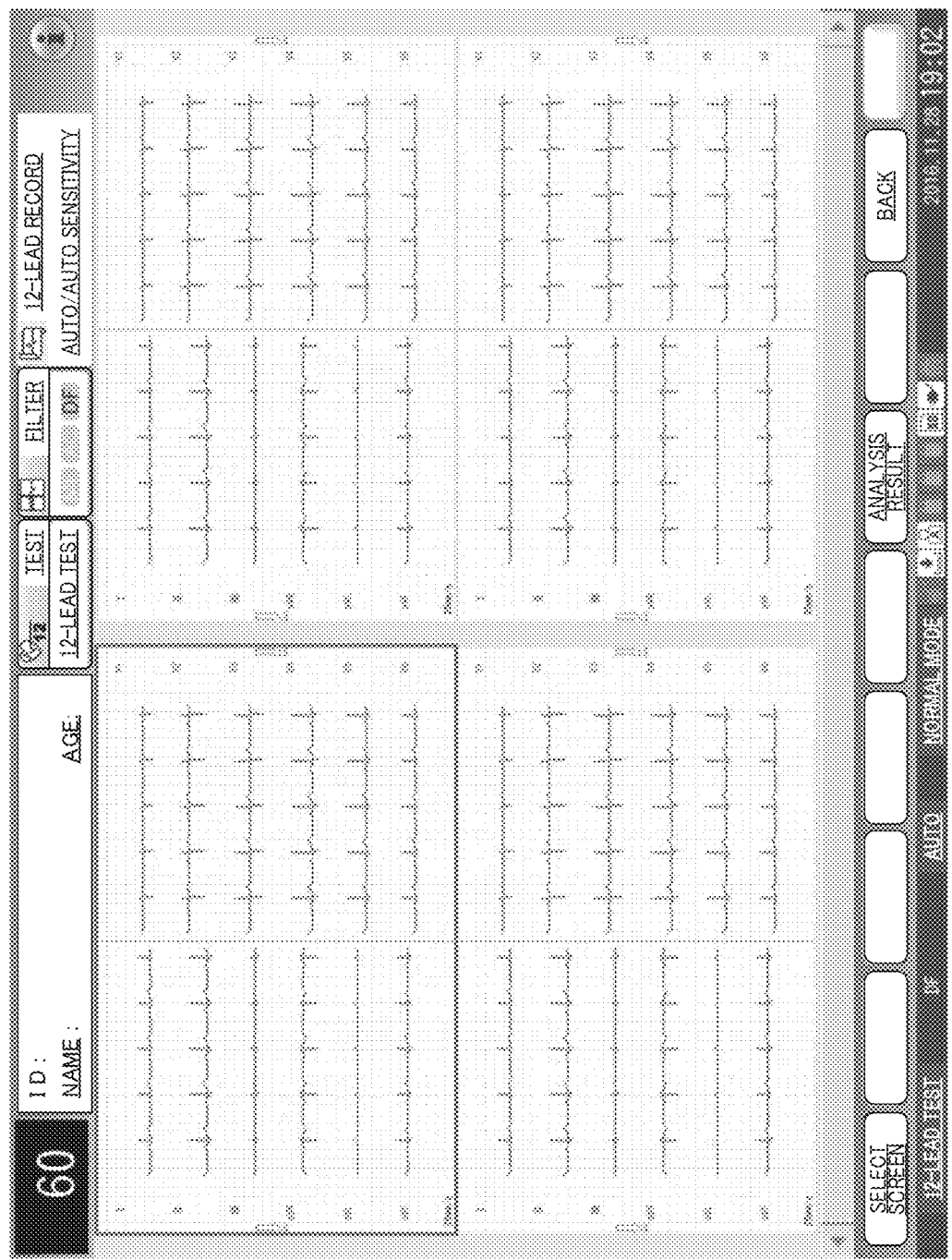
FIG. 9B is a diagram showing a candidate list screen on which the 12-lead electrocardiograms of (six channels×2) are displayed in each candidate region.

The candidate list screen shown in FIG. 9B shows a 12-lead electrocardiogram of (six channels×2) in each candidate region in the continuous mode or coherent mode. It differs from FIG. 9A in that it shows no rhythm waveform.

Figure 9C:
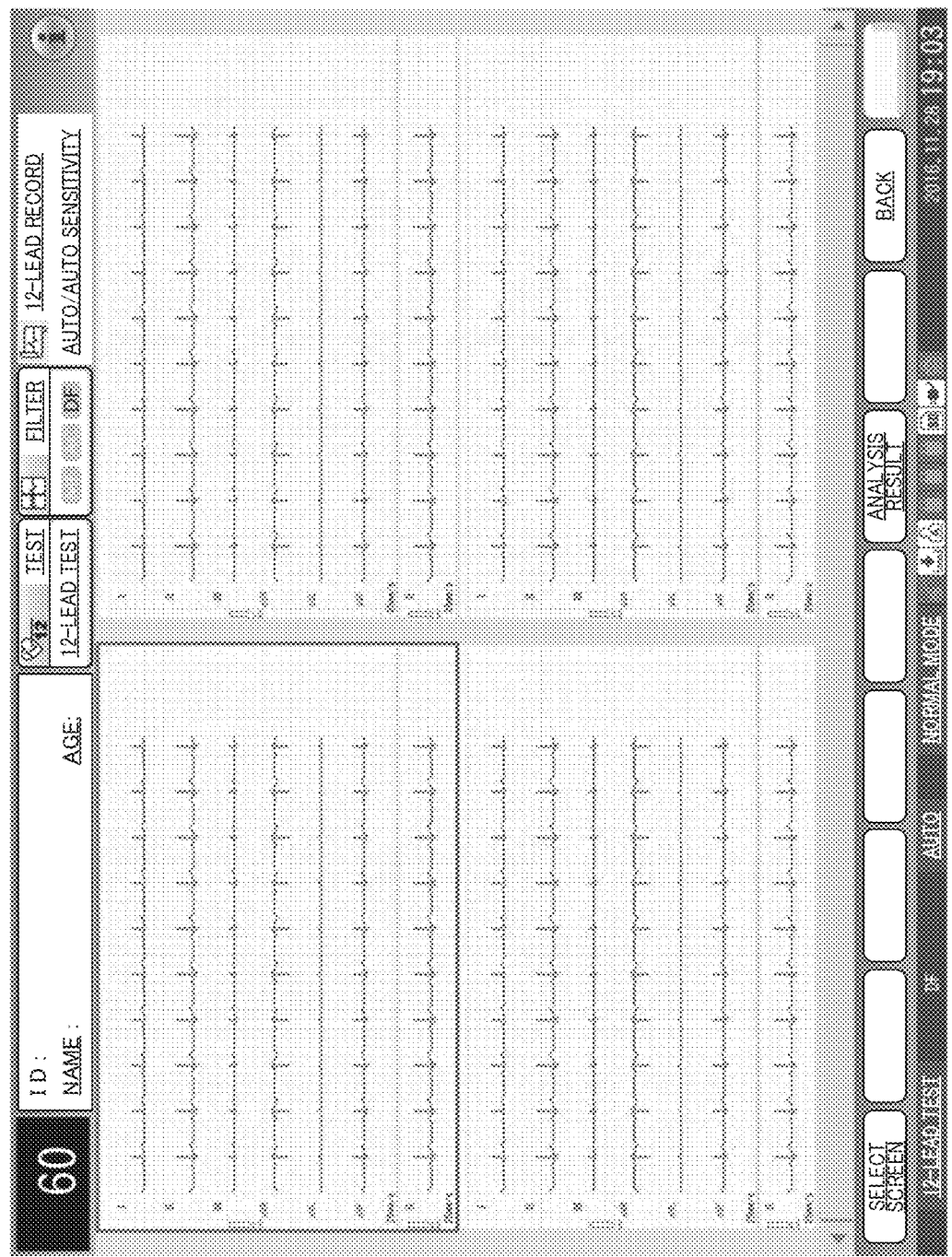
FIG. 9C is a diagram showing a candidate list screen on which the 12-lead electrocardiograms of six channels and the rhythm waveform of one channel are displayed in each candidate region.

The candidate list screen shown in FIG. 9C shows a 12-lead electrocardiogram of six channels and a rhythm waveform of one channel in each candidate region. To be specific, in the candidate list screen shown in FIG. 9C, in each candidate region, the limb lead waveforms I, II, III, aVR, aVL, and aVF of the 12-lead electrocardiogram waveforms are displayed without cutting the waveforms in a partial segment which is cut in the continuous mode (or coherent mode), that is, all the waveforms in a predetermined period (for example, 10 seconds) are displayed.

Figure 9D:
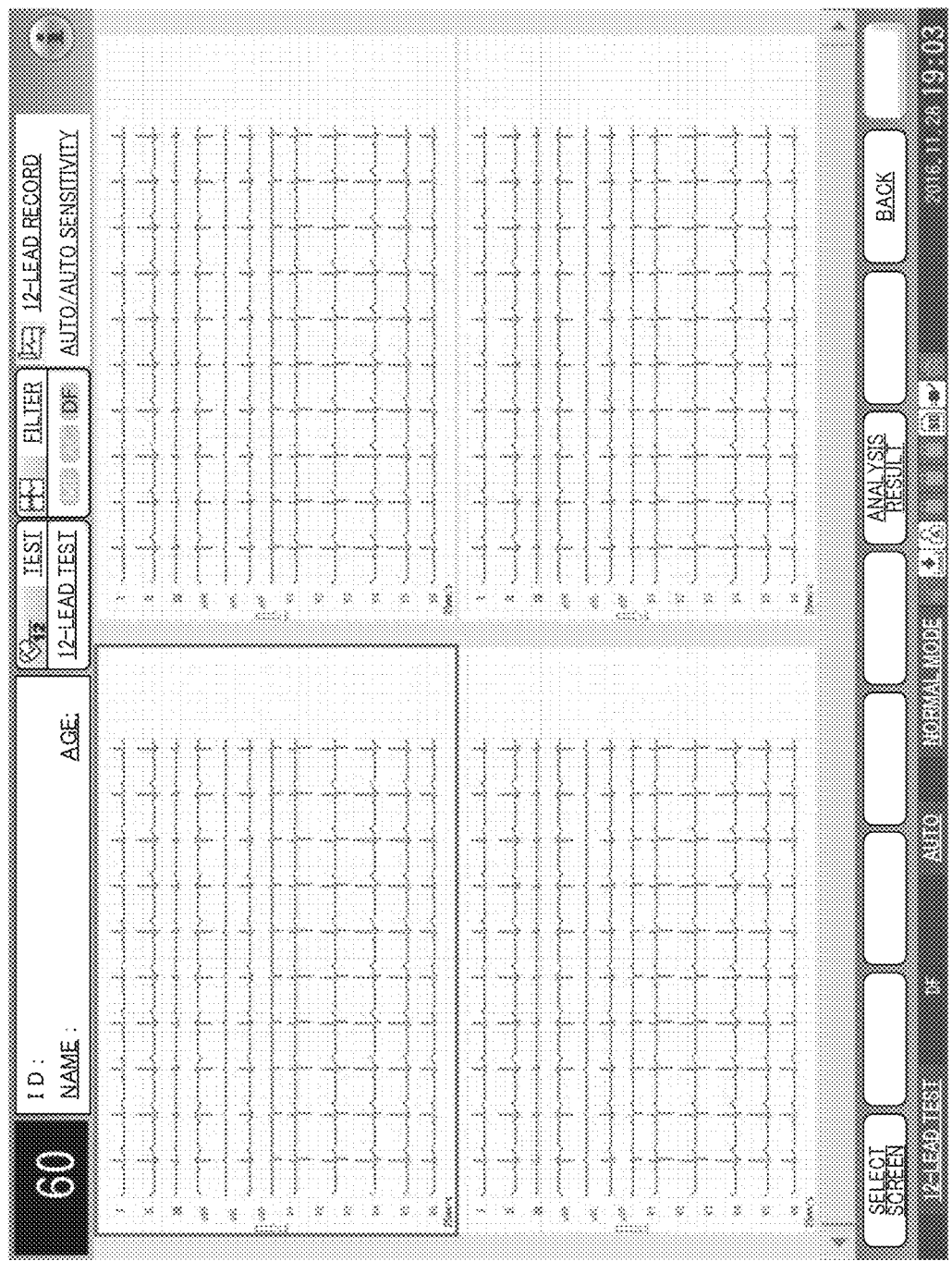
FIG. 9D is a diagram showing a candidate list screen on which the 12-lead electrocardiograms of 12 channels are displayed in each candidate region.

The candidate list screen shown in FIG. 9D shows a 12-lead electrocardiogram of 12 channels in each candidate region. To be specific, in the candidate list screen shown in FIG. 9D, in each candidate region, the limb lead waveforms I, II, III, aVR, aVL, and aVF and chest lead waveforms V1, V2, V3, V4, V5, and V6 of the 12-lead electrocardiogram waveforms are downsized in the sensitivity (waveform amplitude) direction and all vertically aligned, and displayed without cutting the waveforms in a partial segment which is cut in the continuous mode (or coherent mode), that is, all the waveforms in a predetermined period (for example, 10 seconds) are displayed.

<4> Extraction of Candidate Segment From Collected Waveforms

An extraction method of this embodiment for extracting the waveforms in a candidate segment from the collected waveforms temporarily stored in storage section 103 will now be explained. Here, an example in which the collection time is 60 seconds, one candidate segment has a length of 10 seconds, and four candidate segments are extracted will be described. As described above, the collection time can be set in, for example, the range of 30 seconds to 10 minutes (by seconds), and the segment length of each candidate segment can be set in, for example, the range of 8 to 24 seconds. The number of candidate segments to be displayed in a list for analysis is not limited to four.

The extraction methods presented in this embodiment are a method in which extraction is performed excluding noise segments and a method in which extraction is performed including irregular heartbeat waveforms. Here, arithmetic section 101 functions as a candidate waveform extraction section that extracts the electrocardiogram waveforms of a plurality of candidate segments from the collected electrocardiogram waveforms.

<4-1> Method in Which Extraction is Performed Excluding Noise Segments

FIG. 10 is a diagram for explaining a method of extracting the electrocardiogram waveforms of candidate segments excluding noise segments. The waveform at the top of the drawing indicates a collected 60-second waveform temporarily stored in storage section 103. The second row shows that the collected waveform is divided every 10 seconds from the top to form four candidate segments, and the third row shows that candidate segments are extracted excluding noise segments according to this embodiment.

As shown in the second row, in the example in which four candidate segments are formed by dividing every 10 seconds from the top, noise is included in the second, third, and fourth candidate segments. As a result, when the electrocardiogram waveforms of the second, third, and fourth candidate segments are analyzed, the analysis results are greatly affected by noise and the analysis results accurately reflecting the electrocardiogram waveforms cannot therefore be obtained.

For this reason, this embodiment extracts candidate segments excluding noise segments, making it possible to obtain analysis results barely affected by noise and accurately reflecting the electrocardiogram waveforms for all the candidate segments. To be specific, in the collected waveforms that arithmetic section 101 stores in storage section 103, segments in which a waveform that has a frequency extremely higher than that in the assumed electrocardiogram waveform appears (segments in which, for example, alternating current, myoelectricity, or drift occurs), or segments in which an extremely low frequency waveform appears (for example, segments in which noise due to electrode detachment or contact failure is generated) is detected as noise segments, and the electrocardiogram waveforms of the candidate segments are extracted excluding these noise segments. It should be noted that the noise detection method is not limited to this; it is only necessary to detect a waveform different from the assumed human electrocardiogram waveform as noise.

In the example show in FIG. 10, the electrocardiogram waveforms of the four hatched candidate segments of candidates 1 to 4 are extracted by arithmetic section 101 as electrocardiogram waveforms to be displayed on the candidate list screen (FIG. 5) and as the electrocardiogram waveforms of the analysis target.

Figure 11:
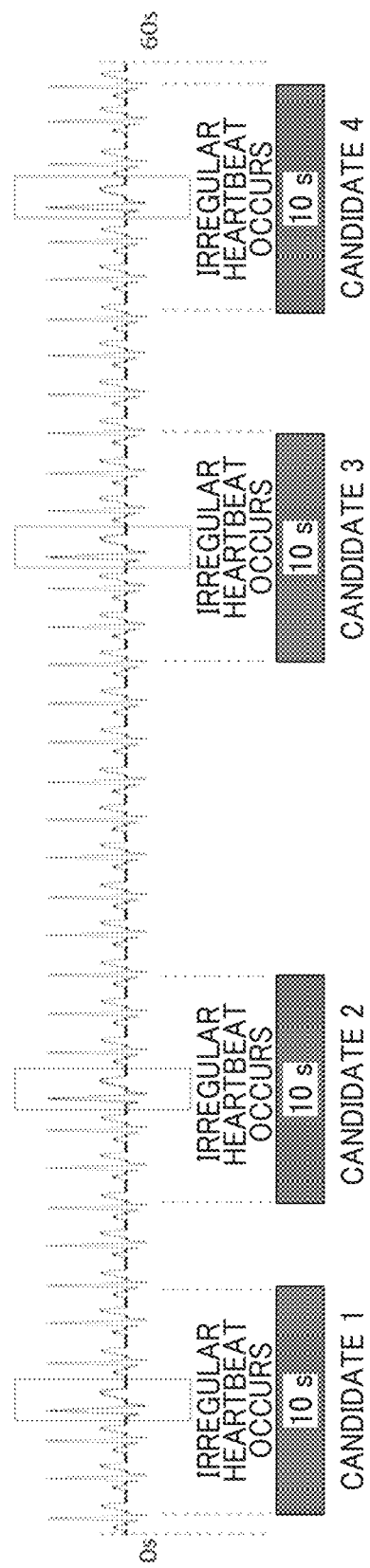
FIG. 11 is a diagram for explaining a method of extracting candidate segments including irregular heartbeat waveforms.

<4-2> Method in Which Extraction is Performed Including Irregular Heartbeat Waveforms FIG. 11 is a diagram for explaining a method of extracting candidate segments including irregular heartbeat waveforms. As shown in FIG. 11, arithmetic section 101 detects the position where an irregular heartbeat is occurring, and the electrocardiogram waveforms of the four hatched candidate segments of candidates 1 to 4 around that position are extracted as electrocardiogram waveforms to be displayed on the candidate list screen (FIG. 5) and as the electrocardiogram waveforms of the analysis target. As described above, display and analysis appropriate for an electrocardiogram examination can be achieved by extracting candidate segments including irregular heartbeat waveforms as candidate segments to be displayed and analyzed.

Here, an irregular heartbeat waveform is preferably disposed at the center of the candidate segment. This is because, with waveforms before and after the irregular heartbeat waveform being provided, whether the irregular heartbeat has suddenly occurred or there has been a sign can be checked referring to the waveforms before and after the irregular heartbeat waveform.

Figure 12:
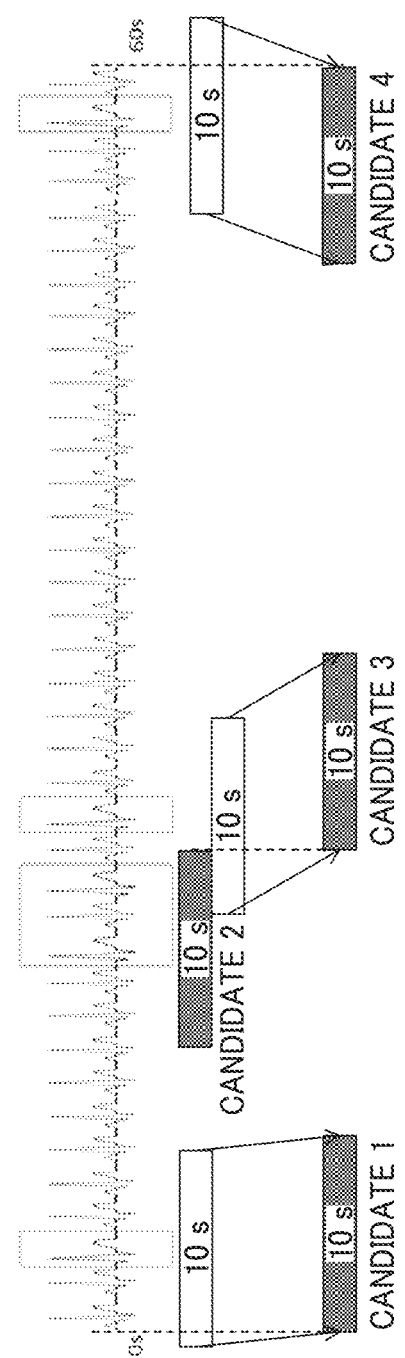
FIG. 12 is a diagram showing an example of shifting a candidate segment when there is a shortage of waveform data or an overlap between candidate segments.

As shown in FIG. 12, to extract candidate segments around the irregular heartbeat position, when the waveform data is insufficient (candidates 1 and 4), the positions of the candidate segments are shifted toward the position where waveform data exists. When the candidate segments overlap (candidates 2 and 3), extraction may be performed shifting the position of any candidate segment toward a direction so that it does not overlap others.

Figure 13:
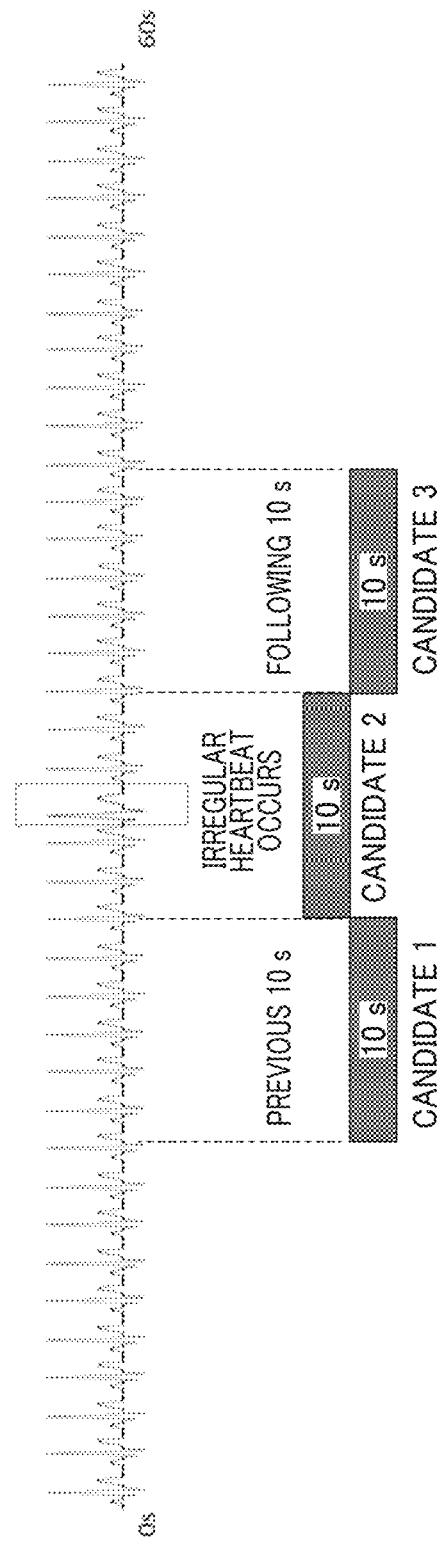
FIG. 13 is a diagram for explaining a method of extracting candidate segments in the case where the number of points where an irregular heartbeat is occurring is smaller than the number of candidate segments to be extracted.

In addition, as shown in FIG. 13, when the number of points where an irregular heartbeat occurs is smaller than the number of candidate segments to be extracted, the segments temporally before and after the candidate segment including an irregular heartbeat (candidate 2 in the case of the drawing) may be extracted as candidate segments (candidates 1 and 3 in the case of the drawing). Only three candidates, candidates 1 to 3, extracted in this way may be displayed or the electrocardiogram waveform of a 0 to 10-second segment in which no irregular heartbeat occurs is extracted and added thereto for display as candidate 4, for example.

<4-3> When Collected Waveform Data is Insufficient

Figure 14:
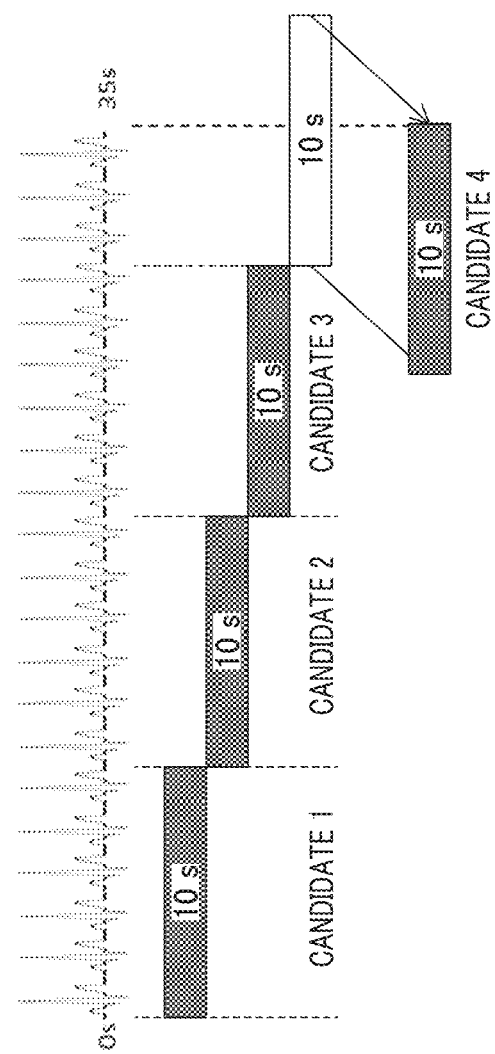
FIG. 14 is a diagram for explaining a method of extracting candidate segments in the case where collected waveform data is insufficient for candidate segments to be extracted.
Figure 15:
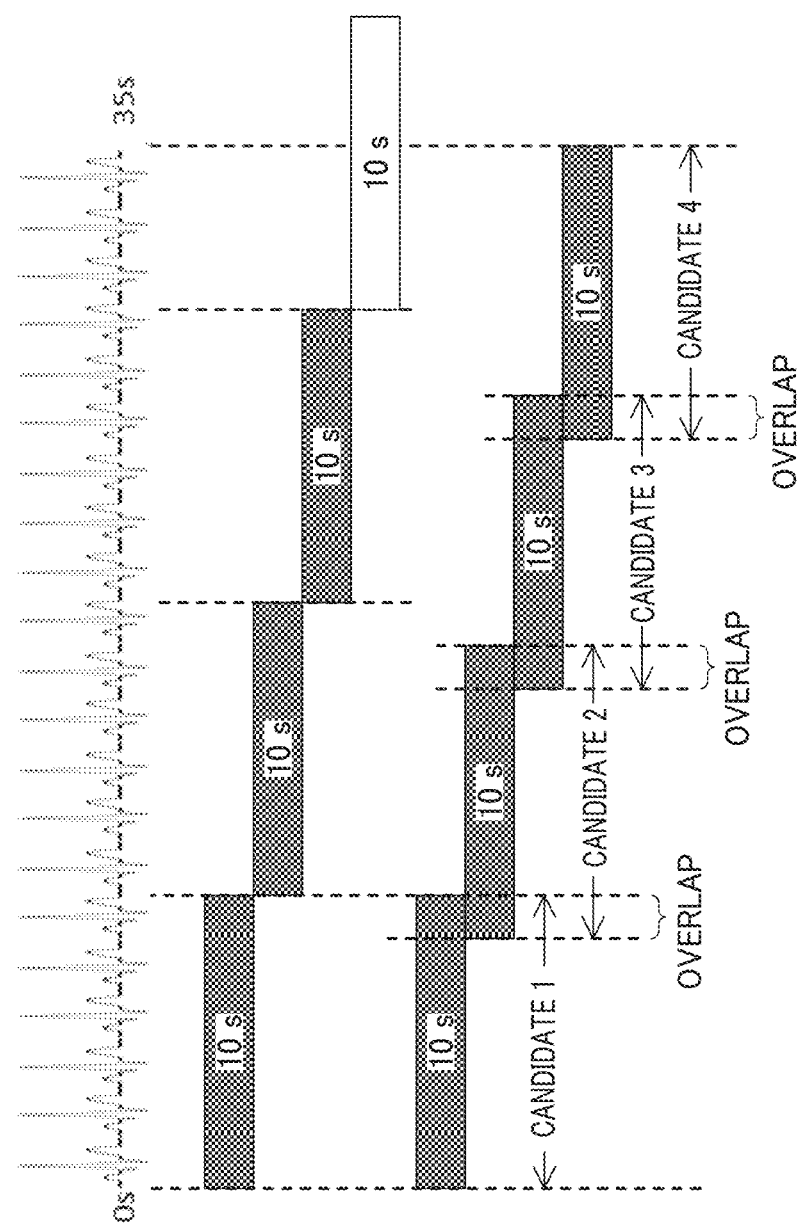
FIG. 15 is a diagram for explaining a method of extracting candidate segments in the case where collected waveform data is insufficient for candidate segments to be extracted.

When the collected waveform data is insufficient for candidate segments to be extracted, the candidate segments may be extracted in such a manner that the candidate segments overlap each other. Examples are shown in FIGS. 14 and 15. In the examples shown in FIGS. 14 and 15, the total time of the candidate segments to be extracted is 10 seconds×4=40 seconds, while the length of the collected waveforms is 35 seconds, which means that the collected waveform data is insufficient.

To address this, in the example shown in FIG. 14, candidate 4 is extracted in such a manner that it overlaps candidate 3. In the example shown in FIG. 15, candidates 1 to 4 are extracted so that parts of all of candidates 1 to 4 overlap by an equal length. When an overlap is not permitted, only three candidates 1 to 3 may be extracted.

<4-4> Priority of Extraction

In practice, there are various situations assumed in extracting a predetermined number of candidate segments from a collected waveform having a length predetermined by settings. In an example assumed situation, the number of irregular heartbeat waveforms in the collected waveform is larger than that of candidate segments. Accordingly, the priority of extraction of candidate segments will now be explained.

In this embodiment, candidate segments are extracted in the following order of priority: (i) noise elimination, (ii) overlap prohibition, and (iii) extraction centered around an irregular heartbeat, for example. In other words, since the presence of noise precludes the acquisition of correct analysis results, noise elimination is given top priority. When an overlap occurs during extraction centered around an irregular heartbeat, overlap prohibition is prioritized over extraction centered around an irregular heartbeat. This is the case shown in FIG. 12.

In addition, when the number of irregular heartbeats in the collected waveforms is larger than the number of candidate segments to be extracted, it is preferable to preferentially extract segments with irregular heartbeats of higher severity. For example, in the case where the number of candidate segments to be extracted is four, while the collected waveforms include six irregular heartbeats in which two have high severity, two have medium severity, and two have low severity, it is preferable to preferentially extract four candidate segments with higher severity, that is, two candidate segments having irregular heartbeats of high severity and two candidate segments having irregular heartbeats of medium severity. When the two irregular heartbeats of high severity are of the same type, it is acceptable that either one of them is regarded as a candidate segment according to the priority based on an element other than severity, and four candidate segments consisting of the same, two with middle severity, and one with low severity are extracted.

Needless to say, which parameter should be preferably prioritized may differ depending on the medical site and the like, and the priority may be therefore settable.

As described above, in electrocardiograph 100 of this embodiment, when the user touches analysis result button B1 on the candidate list screen shown in FIG. 5, an analysis result screen for the waveform enclosed by selection frame W1 is displayed.

Aside from that, in electrocardiograph 100 of this embodiment, while an electrocardiogram waveform is displayed on the screen, the analysis results related to the displayed electrocardiogram waveform can be displayed on the same screen as that showing the electrocardiogram waveform.

Figure 16:
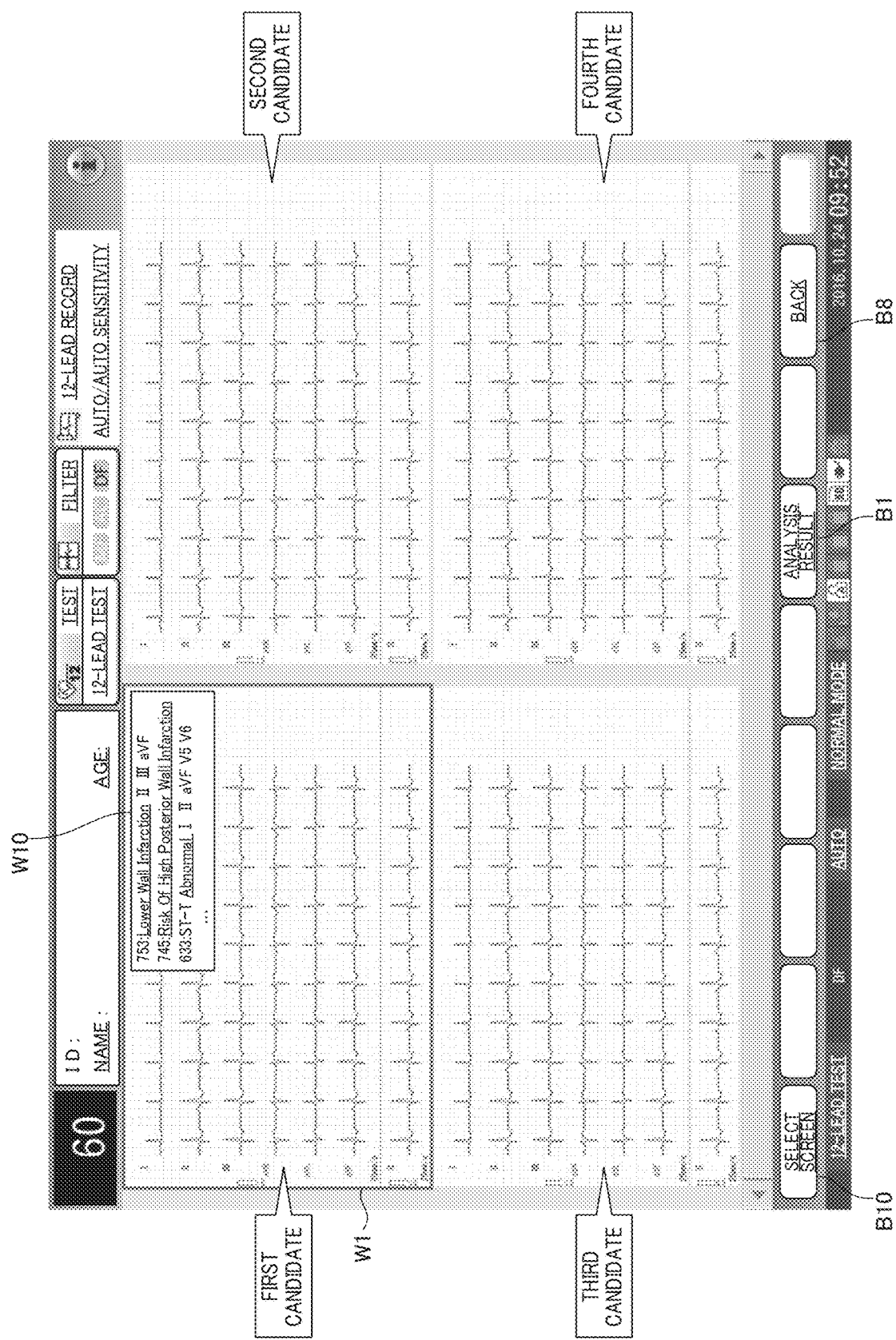
FIG. 16 is a diagram showing a screen on which a simple window for displaying the analysis results is displayed.
Figure 17:
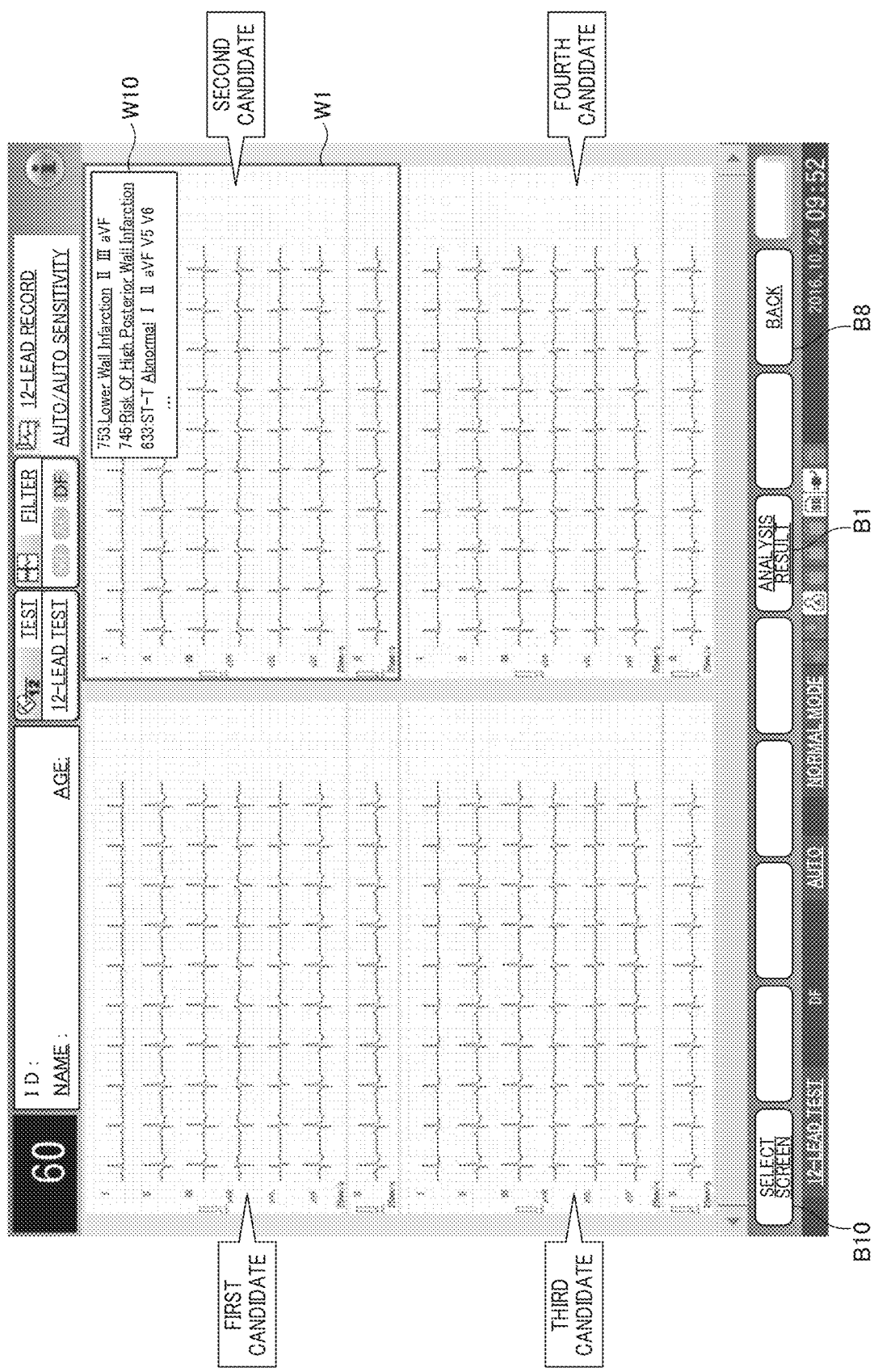
FIG. 17 is a diagram showing a screen on which a simple window for displaying the analysis results is displayed.

FIGS. 16 and 17 show the display example. As shown in FIG. 16, when the user long-presses the display area of the first candidate with a finger (that is, continues touching for a predetermined time or more), the display area of the first candidate is enclosed by selection frame W1, simple window W10 is displayed, and the analysis results related to the waveforms of the first candidate segment is displayed in this simple window W10. The analysis results displayed in simple window W10 are analysis findings related to the waveforms of the first candidate segment. Note that what is displayed in simple window W10 may be other analysis results such as measurement values and representative waveforms. Moving the finger off the touch screen closes simple window W10.

The analysis results displayed in simple window W10 are sorted in the order of severity. Therefore, when there are many analysis results, only the analysis results with higher severity are displayed in simple window W10. Note that the user may be able to set which analysis result is displayed in simple window W10.

Here, simple window W10 is preferably translucent. This allows the electrocardiogram waveforms in the position of simple window W10 to be translucent even when simple window W10 is displayed in the area enclosed by selection frame W1. Simple window W10 should not necessarily be displayed in selection frame W1.

Further, the method of displaying simple window W10 is not limited to long-pressing touch screen 121; for example, simple window W10 may be displayed by moving the pointer into any of the display areas of the first to fourth candidates and clicking or double-clicking with a mouse button in that position. In this case, closing of simple window W10 may also be done with a mouse.

With the configuration in which long-pressing touch screen 121 with a finger opens simple window W10 and moving the finger off touch screen 121 closes simple window W10 as in the embodiment, a window can be shown and hidden by one action, which is advantageous because the analysis results of a plurality of candidate segments can be viewed quickly.

Similarly, as shown in FIG. 17, when the user long-presses the display area of the second candidate with a finger, the display area of the second candidate is enclosed by selection frame W1, simple window W10 is displayed, and the analysis results related to the waveforms of the second candidate segment are displayed in this simple window W10. Similarly for the third and fourth candidates, simple analysis results can be displayed in simple window W10 by the same operation.

Thus, in this embodiment in which simple window W10 showing the analysis results related to electrocardiogram waveforms is displayed on the screen showing the electrocardiogram waveforms, the analysis results can be checked without switching the screen. As a result, the examination results can be checked with fewer procedures, and electrocardiogram waveforms and the related analysis results can be compared on the same screen.

Moreover, since the electrocardiogram waveforms of a plurality of candidate segments are displayed on the same screen so that the analysis results related to the electrocardiogram waveforms of each candidate segment can be selectively displayed on the screen showing the electrocardiogram waveforms of a plurality of candidate segments, it is possible to check the analysis findings while comparing a plurality of recorded waveforms in the state where the recorded waveforms are displayed on the same screen, which allows the examination results to be checked with fewer procedures.

In this embodiment, among the electrocardiogram waveforms of the plurality of candidate segments displayed on the same screen, only the analysis results related to the electrocardiogram waveforms of one candidate segment selected by the user are displayed on the same screen. Alternatively, the analysis results related to the electrocardiogram waveforms of two or more candidate segments selected by the user may be displayed on the same screen.

<5> Collective Movement of Electrocardiogram Waveforms

As described above, the electrocardiogram waveforms of the plurality of candidate segments displayed on the candidate list screen are extracted by arithmetic section 101. The electrocardiogram waveforms of the candidate segments correspond to the waveforms of segments that have been determined to be appropriate for analysis by arithmetic section 101, as described above.

Figure 18:
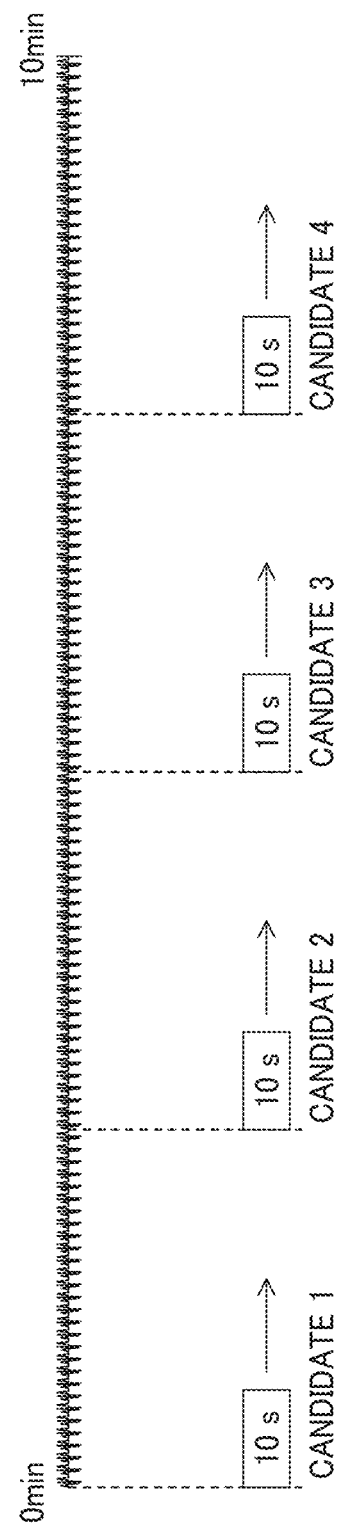
FIG. 18 is a diagram showing an example of the position in which an electrocardiogram waveform is extracted in each segment in the case where electrocardiogram waveforms are collectively moved.

This embodiment has, in addition to the mode in which candidate segments appropriate for such analysis are set, a waveform collective-movement mode for extracting segments appropriate for waveform check or waveform comparison of/between electrocardiogram waveforms. Arithmetic section 101, which serves as an electrocardiogram waveform extracting section, extracts candidates 1 to 4 as shown in FIG. 18, for example, when the waveform collective-movement mode is set through an operation by the user. In the example shown in FIG. 18, an electrocardiogram waveform having a length of 10 minutes is collected in storage section 103, and candidates 1 to 4 each having a segment length of 10 seconds are extracted from this electrocardiogram waveform. Here, the intervals between candidates 1 to 4 are equal and are 2.5 minutes in the example shown in FIG. 18. In particular, candidate 1 is an electrocardiogram waveform ranging from 0 seconds to 10 seconds, candidate 2 is an electrocardiogram waveform ranging from 2 minutes 30 seconds to 2 minutes 40 seconds, candidate 3 is an electrocardiogram waveform ranging from 5 minutes to 5 minutes 10 seconds, and candidate 4 is an electrocardiogram waveform ranging from 7 minutes 30 seconds to 7 minutes 40 seconds. Strictly speaking, the heads of the adjacent segments among the plurality of segments are away from each other by the time length (2.5 minutes in the example shown in the drawing) obtained by dividing the time length of the collected electrocardiogram waveform (10 minutes in the example shown in the drawing) by the number of segments (four in the example shown in the drawing).

Figure 19A:
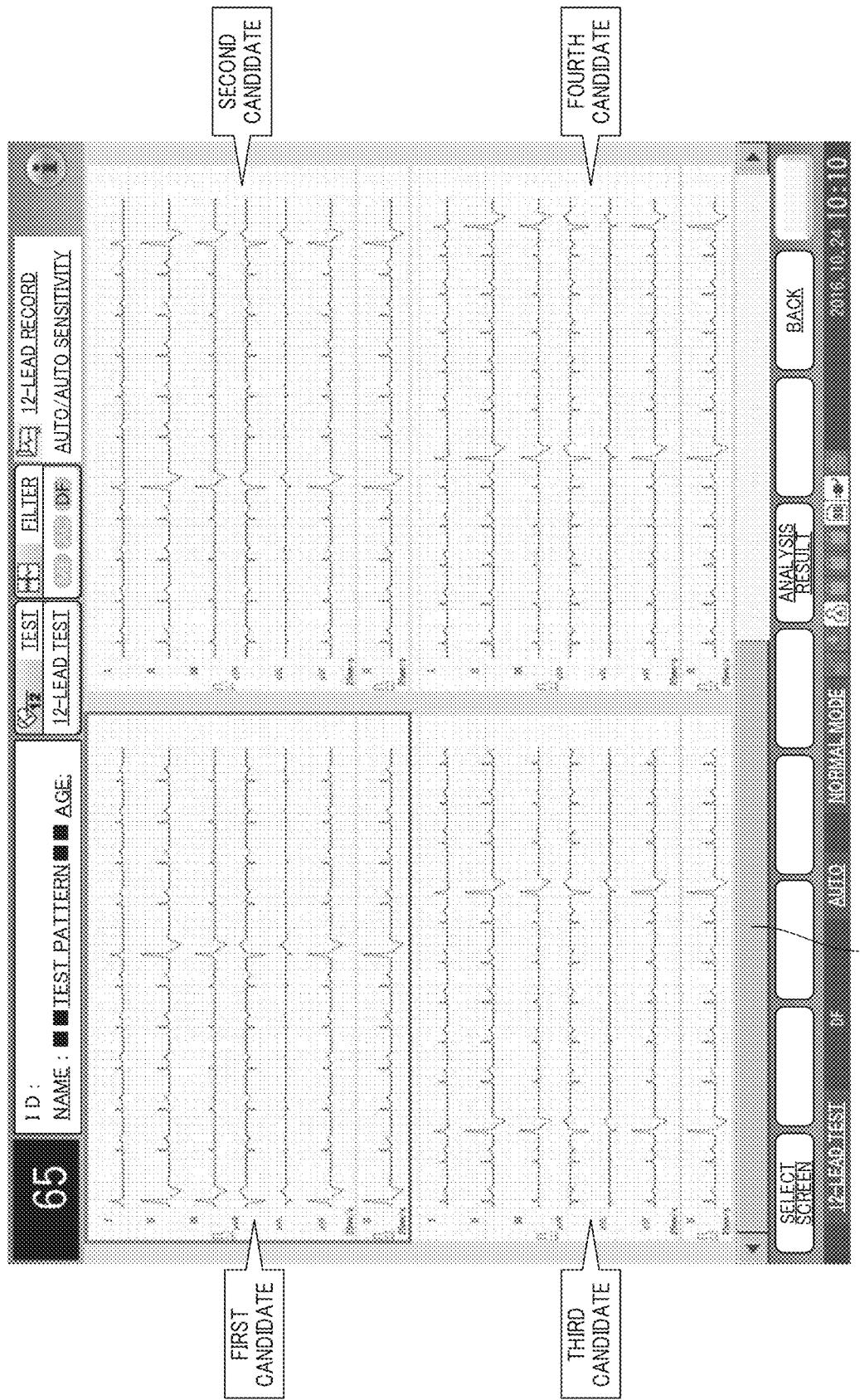
FIG. 19A is a diagram for explaining the collective movement of electrocardiogram waveforms.
Figure 19B:
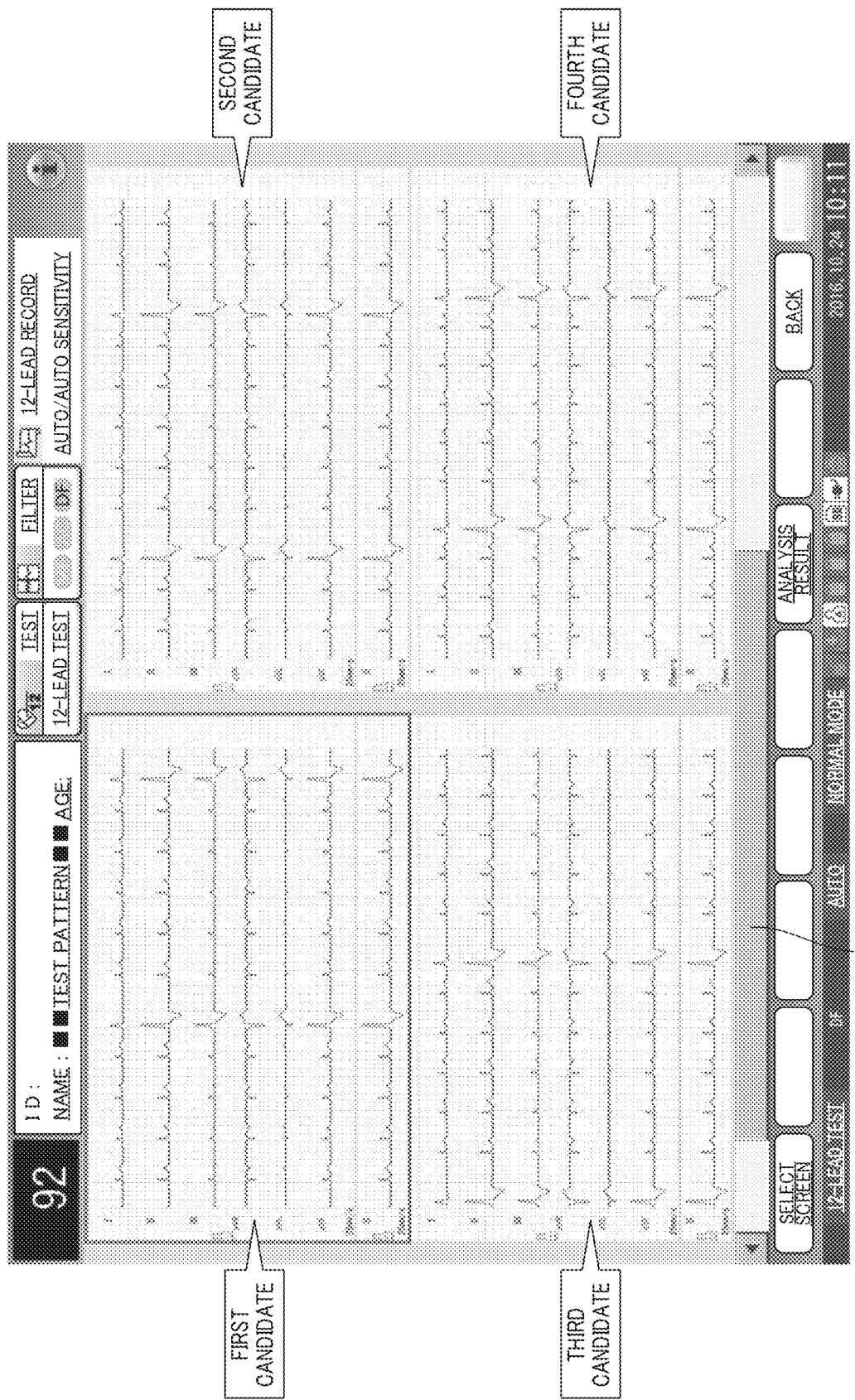
FIG. 19B is a diagram for explaining the collective movement of electrocardiogram waveforms.
Figure 19C:
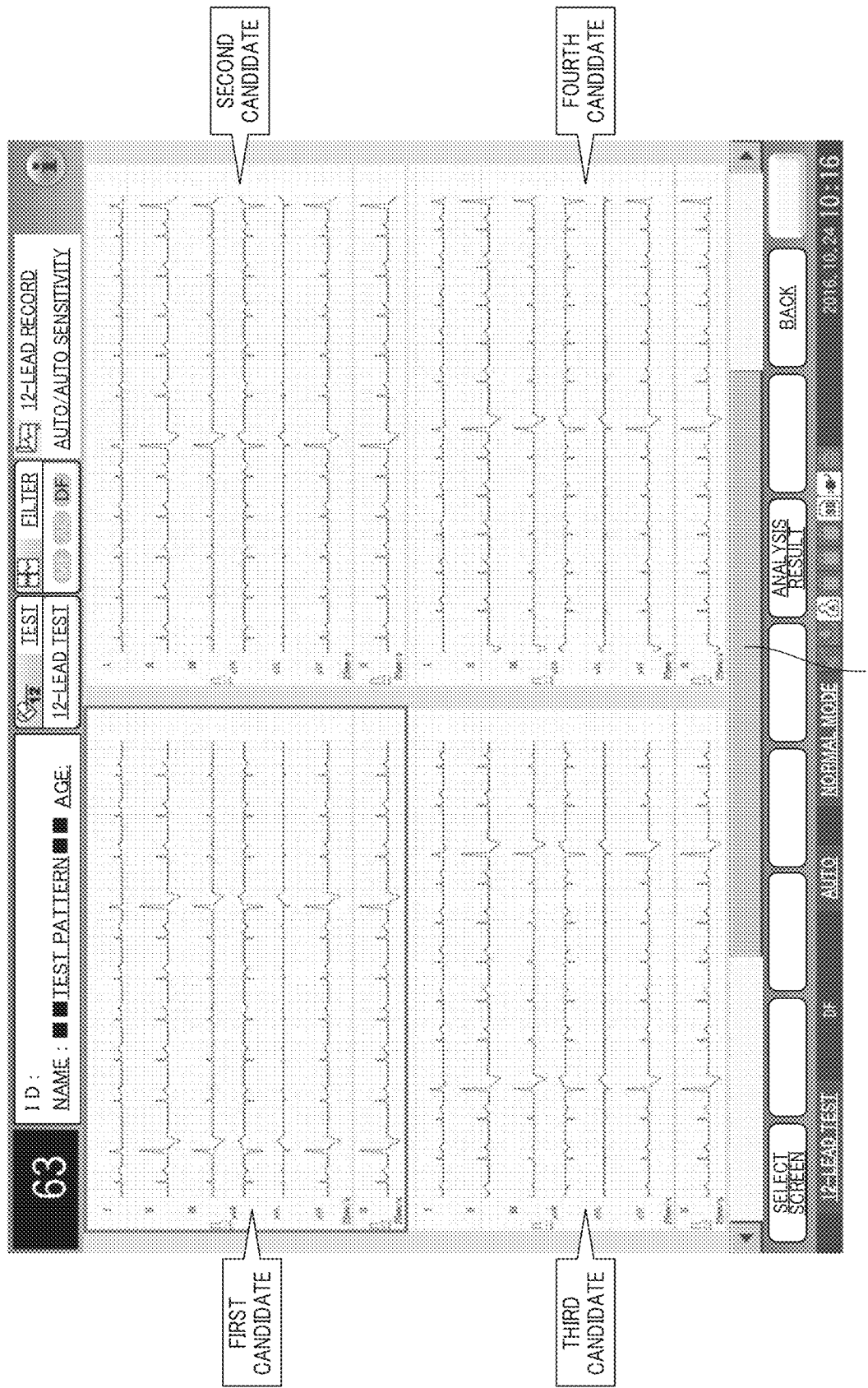
FIG. 19C is a diagram for explaining the collective movement of electrocardiogram waveforms.
Figure 19D:
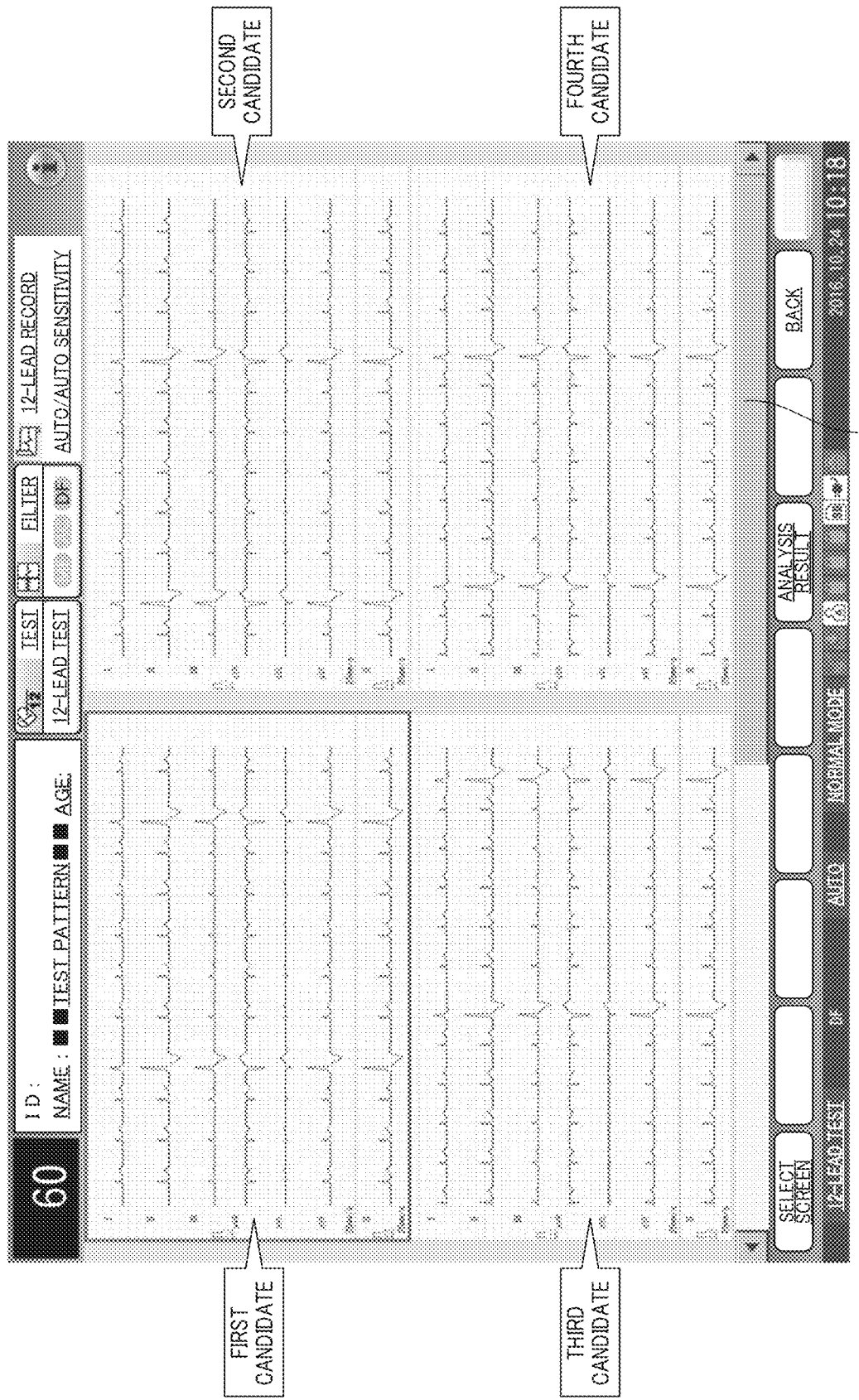
FIG. 19D is a diagram for explaining the collective movement of electrocardiogram waveforms.

FIG. 19A shows the state where the electrocardiogram waveforms of candidates 1 to 4 in FIG. 18 are displayed on touch screen 121. Moving scroll bar S1 in the state shown in FIG. 19A to the right so that the screen switches from the state shown in FIG. 19A to the state shown in FIG. 19B, to the state shown in FIG. 19C, and then to the state shown in FIG. 19D moves all the electrocardiogram waveforms of the first to fourth candidates to the right according to the amount of the travel of scroll bar S1. To be specific, arithmetic section 101 or display/print control section 106 shifts the positions where the electrocardiogram waveforms of the first to fourth candidates are extracted in the direction indicated by the arrow in FIG. 18 according to the movement of scroll bar S1. Needless to say, moving scroll bar S1 to the left moves all the electrocardiogram waveforms of the first to fourth candidates to the left according to the amount of the travel of scroll bar S1.

As described above, in this embodiment, the electrocardiogram waveforms of a plurality of segments (candidates 1 to 4) are extracted from the collected electrocardiogram waveforms, and the extracted electrocardiogram waveforms of the plurality of segments are displayed on one screen. Since the positions where the electrocardiogram waveforms of the plurality of segments are extracted are equally shifted in the time direction by the amount dependent on the operation by the user, the electrocardiogram waveforms of the candidate segments can be collectively moved equally in the time direction according to the operation by the user.

As a result, the substantial travel amount in the time direction caused by an operation can be increased, and the number of electrocardiogram waveforms that are made visible to the user with an operation can be increased from in the case where the electrocardiogram waveform of each segment is moved independently. For example, in the examples shown in FIGS. 19A to 19D, since the four electrocardiogram waveforms are collectively moved in the time direction, the travel amount of each electrocardiogram waveform in the time direction caused by an operation can be quadrupled from in the case where the electrocardiogram waveform of each candidate is moved independently.

This is particularly effective when the collection time is long. In particular, when the collection time is long, it takes time to visually check all the collected electrocardiogram waveforms. In such a case, when the electrocardiogram waveforms of a plurality of segments are displayed on the same screen and are collectively moved in the time direction according to one operation as in this embodiment, the time required to check all the collected electrocardiogram waveforms can be shortened.

Further, in this embodiment, even in the case of an electrocardiogram waveform which is collected with a long time, for example, 10 minutes, even electrocardiogram waveform parts temporally away from each other, such as the electrocardiogram waveform part near the start of the collection and the electrocardiogram waveform part near the end of the collection, can be displayed on the same screen and the electrocardiogram waveform can be checked while comparing them with each other. As a result, even when the collected electrocardiogram waveform extends for a long time as in a stress test, the electrocardiogram waveform can be checked while comparing the electrocardiogram waveform parts near the start and end.

Further, the processing according to this embodiment is essentially to equally shift the positions where the electrocardiogram waveforms of the plurality of segments are extracted in the time direction by the amount dependent on the operation by the user when the extracted electrocardiogram waveforms of the plurality of segments are displayed on one screen. Such processing is also effective in procedures other than waveform check and waveform comparison for a long-time electrocardiogram waveform like that in this embodiment.

For example, when segments including the same type of irregular heartbeat waveforms are extracted as the collected plurality of segments and are aligned in tandem on the screen so that the centers of the irregular heartbeats are vertically aligned, a temporally different plurality of irregular heartbeat waveforms of the same type are aligned in tandem and are collectively moved equally in the time direction on the screen according to the operation by the user. This allows the user to view and compare changes in a plurality of irregular heartbeats on the screen.

As described above, the collective movement process for an electrocardiogram waveform according to this embodiment is widely effective in checking changes in the time direction in the electrocardiogram waveform at different points in time while comparing them with each other.

<6> Conclusions

As described above, this embodiment displays simple window W10 that shows electrocardiogram waveforms and the analysis results related to the electrocardiogram waveforms at the same time, allowing the analysis results to be checked without switching the screens. This makes it possible to check the examination results with fewer procedures and compare the electrocardiogram waveforms and the related analysis results on the same screen at the same time.

Moreover, since the electrocardiogram waveforms of a plurality of candidate segments (analysis unit segments) are displayed on one screen so that the analysis results related to the electrocardiogram waveforms of each candidate segment can be selectively displayed on the screen showing the electrocardiogram waveforms of a plurality of candidate segments, it is possible to check the analysis findings while comparing the waveforms of the analysis segments in the state where the waveforms of the plurality of analysis unit segments are displayed on one screen, which allows the examination results to be checked with fewer procedures.

The above embodiments merely show specific examples for implementing the present invention and the technical scope of the present invention should not be construed as being limited by them. In other words, the present invention can be implemented in various modes without departing from the spirit or main features of the present invention.

For example, although the above embodiments describe the case where the electrocardiogram analyzing apparatus and electrocardiogram waveform display method of the present invention are implemented using electrocardiograph 100, the electrocardiogram analyzing apparatus and electrocardiogram waveform display method of the present invention can also be implemented using devices having an arithmetic section and a display section other than electrocardiographs.

Further, each processing in the electrocardiogram analyzing apparatus and electrocardiogram waveform display method of the present invention can also be implemented when a device having an arithmetic section and a display section executes a program. For example, a program for implementing each processing in the electrocardiogram analyzing apparatus and electrocardiogram waveform display method of the present invention may be recorded in a computer-readable recording medium, such as a memory, disc, tape, CD, or DVD, so that the computer of the device having the arithmetic section and the display section may execute each processing in the above embodiments by reading the program.

The disclosure of the specification, accompanying drawings, and abstract included in Japanese Patent Application No. 2016-233323 filed on Nov. 30, 2016 is incorporated in this application by reference.

INDUSTRIAL APPLICABILITY

The present invention is applicable to, for example, an electrocardiograph having a function of automatically analyzing electrocardiograms.

REFERENCE SIGNS LIST

100 Electrocardiograph
101 Arithmetic section
102 Measurement section
103 Storage section
104 Input keys
105 Printer section
106 Display/print control section
110 Body
120 Display section
121 Touch screen
A1 Finding
A2 Finding commentary
A3 Measurement value
W1 Selection frame
W10 Simple window

What is claimed is:

1. An electrocardiogram waveform display method used for an electrocardiogram analyzing apparatus, the method comprising:
    a step of storing measured electrocardiogram waveform;
    an analysis candidate segment extracting step of extracting a plurality of analysis candidate segments from the stored electrocardiogram waveform, each analysis candidate segment including electrocardiographic waveforms for multiple heartbeats;
    a first display step of displaying the plurality of analysis candidate segments on a screen;
    an analysis step of analyzing the analysis candidate segment selected by a user among the plurality of analysis candidate segments displayed on the screen; and
    a second display step of displaying an analysis result obtained in the analysis step on the same screen as the screen on which the plurality of analysis candidate segments are displayed,
    wherein, the analysis candidate segment extracting step includes extracting the plurality of analysis candidate segments such that parts of the plurality of analysis candidate segments overlap each other and other parts of the of the plurality of analysis candidate segments do not overlap.

2. The electrocardiogram waveform display method according to claim 1, wherein in the second display step, the analysis result is displayed in a translucent window.

3. The electrocardiogram waveform display method according to claim 1, wherein in the second display step, the analysis results are sorted in descending order of severity when displayed.

4. The electrocardiogram waveform display method according to claim 1, wherein in the second display step, the analysis result is displayed while the user long-presses the screen.

5. The electrocardiogram waveform display method according to claim 1, wherein the plurality of analysis candidate segments extracted in the extracting step are ones from which a noise segment is removed and/or which include an irregular heartbeat waveform.

6. An electrocardiogram analyzing apparatus, comprising:
a display section;
a display control section;
a storage section that stores measured electrocardiogram waveforms;
a user operation section; and
an arithmetic section that acquires an analysis result by analyzing an analysis candidate segment which includes electrocardiogram waveforms for multiple heartbeats, wherein
the display control section displays on a screen a plurality of analysis candidate segments which are extracted from the stored electrocardiogram waveform and which are at least partially overlapped each other and at least partially non-overlapped each other in time direction,
the arithmetic section analyzes the analysis candidate segment selected by a user among the plurality of analysis candidate segments displayed on the screen,
the display control section further displays the analysis result obtained by the arithmetic section on the same screen as the screen on which the plurality of analysis candidate segments are displayed.

7. The electrocardiogram waveform display method according to claim 1, wherein in the first display step, one screen is divided into a plurality of areas, and the analysis candidate segments extracted in the extracting step are displayed in each divided area.

8. The electrocardiogram waveform display method according to claim 1, wherein the analysis candidate segments displayed in the first display step include temporally discontinuous segments.

9. The electrocardiogram waveform display method according to claim 1, wherein;
in the first display step, one screen is divided into a plurality of areas, and the analysis candidate segments extracted in the extracting step are displayed in each divided area;
in the analysis step, analyzing the analysis candidate segment selected by a user among the plurality of analysis candidate segments displayed on the screen; and
in the second display step, displaying the analysis result obtained in the analysis step in the divided area selected by the user in the analysis step.

10. The electrocardiogram analyzing apparatus according to claim 6, wherein the display control section divides one screen into a plurality of areas, and displays the analysis candidate sections which are at least partially overlapped each other and at least partially non-overlapped each other in time direction, in each divided area.

11. The electrocardiogram waveform display method according to claim 1, wherein;
the analysis candidate segment extracting step includes extracting the plurality of analysis candidate segments such that the overlapping parts of the plurality of analysis candidate segments overlap by an equal length.

12. The electrocardiogram analyzing apparatus according to claim 6, wherein the display control section displays the plurality of analysis candidate segments such that the overlapping parts of the plurality of analysis candidate segments overlap by an equal length.

* * * * *